US008383269B2

(12) United States Patent
Scott et al.

(10) Patent No.: US 8,383,269 B2
(45) Date of Patent: *Feb. 26, 2013

(54) NEGATIVE-LIMITED LITHIUM-ION BATTERY

(75) Inventors: Erik R. Scott, Maple Grove, MN (US); Gaurav Jain, Edina, MN (US); Kevin W. Eberman, St. Paul, MN (US); Craig L. Schmidt, Eagan, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/086,294

(22) Filed: Apr. 13, 2011

(65) Prior Publication Data

US 2011/0281148 A1 Nov. 17, 2011

Related U.S. Application Data

(63) Continuation of application No. 12/240,652, filed on Sep. 29, 2008, now Pat. No. 7,927,742, which is a continuation-in-part of application No. 10/979,040, filed on Oct. 29, 2004, now Pat. No. 7,811,705, and a continuation-in-part of application No. 12/112,979, filed on Apr. 30, 2008.

(51) Int. Cl.
*H01M 4/58* (2010.01)
(52) U.S. Cl. .............. 429/231.1; 429/231.3; 429/231.5; 429/332; 429/330; 429/94; 429/249; 429/247; 429/129; 429/96; 429/163
(58) Field of Classification Search .............. 429/231.5, 429/332, 330, 94, 249, 247, 129, 96, 163, 429/231.1, 231.3
See application file for complete search history.

(56) References Cited

U.S. PATENT DOCUMENTS

| 3,308,306 | A | 3/1967 | Bagno |
| 3,462,303 | A | 8/1969 | Reber |
| 3,791,867 | A | 2/1974 | Broadhead et al. |
| 3,864,167 | A | 2/1975 | Broadhead et al. |
| 3,898,096 | A | 8/1975 | Heredy et al. |
| 4,009,052 | A | 2/1977 | Whittingham |
| 4,048,397 | A | 9/1977 | Rothbauer |
| 4,049,887 | A | 9/1977 | Whittingham |
| 4,113,921 | A | 9/1978 | Goldstein et al. |
| 4,194,062 | A | 3/1980 | Carides et al. |
| 4,202,702 | A | 5/1980 | Nuss |
| 4,340,652 | A | 7/1982 | Raistrick et al. |
| 4,446,212 | A | 5/1984 | Kaun |
| 4,464,447 | A | 8/1984 | Lazzari et al. |

(Continued)

FOREIGN PATENT DOCUMENTS

| EP | 0 732 761 A1 | 9/1996 |
| EP | 0 982 790 A1 | 3/2000 |

(Continued)

OTHER PUBLICATIONS

Guyomard et al., New Amorphous Oxides as High Capacity Negative Electrodes for Lithium 6 Batteries the LixMV04 (M=Ni, Co, Cd, Zn; 1 <x<8) Series, Journal of Power Sources 68, 1997, 6 pages.

(Continued)

*Primary Examiner* — Laura Weiner
(74) *Attorney, Agent, or Firm* — Foley & Lardner LLP

(57) ABSTRACT

A rechargeable lithium-ion battery includes a positive electrode having a first capacity and a negative electrode having a second capacity that is less than the first capacity such that the battery has a negative-limited design. The negative electrode includes a lithium titanate active material. A liquid electrolyte that includes a lithium salt dissolved in at least one non-aqueous solvent a porous polymeric separator are located between the positive electrode and negative electrode. The separator is configured to allow lithium ions to flow through the separator.

24 Claims, 8 Drawing Sheets

U.S. PATENT DOCUMENTS

| | | |
|---|---|---|
| 4,507,371 A | 3/1985 | Thackeray et al. |
| 4,547,442 A | 10/1985 | Besenhard et al. |
| 4,555,456 A | 11/1985 | Kanehori et al. |
| 4,668,595 A | 5/1987 | Yoshino et al. |
| 4,764,437 A | 8/1988 | Kaun |
| 4,830,939 A | 5/1989 | Lee et al. |
| 5,053,297 A | 10/1991 | Yamahira et al. |
| 5,077,151 A | 12/1991 | Yasuda et al. |
| 5,147,737 A | 9/1992 | Post et al. |
| 5,147,739 A | 9/1992 | Beard |
| 5,160,712 A | 11/1992 | Thackeray et al. |
| 5,162,170 A | 11/1992 | Miyabayashi et al. |
| 5,162,178 A | 11/1992 | Ohsawa et al. |
| 5,169,736 A | 12/1992 | Bittihn et al. |
| 5,176,969 A | 1/1993 | Miyabayashi et al. |
| 5,187,033 A | 2/1993 | Koshiba |
| 5,187,035 A | 2/1993 | Miyabayashi et al. |
| 5,196,279 A | 3/1993 | Tarascon |
| 5,264,201 A | 11/1993 | Dahn et al. |
| 5,284,721 A | 2/1994 | Beard |
| 5,296,318 A | 3/1994 | Gozdz et al. |
| 5,300,373 A | 4/1994 | Shackle |
| 5,322,746 A | 6/1994 | Wainwright |
| 5,331,268 A | 7/1994 | Patino et al. |
| 5,340,666 A | 8/1994 | Tomantschger et al. |
| 5,401,598 A | 3/1995 | Miyabayashi et al. |
| 5,411,537 A | 5/1995 | Munshi et al. |
| 5,418,090 A | 5/1995 | Koksbang et al. |
| 5,478,668 A | 12/1995 | Gozdz |
| 5,498,489 A | 3/1996 | Dasgupta et al. |
| 5,510,212 A | 4/1996 | Delnick et al. |
| 5,525,441 A | 6/1996 | Reddy et al. |
| 5,545,468 A | 8/1996 | Koshiba et al. |
| 5,547,785 A | 8/1996 | Yumiba et al. |
| 5,569,553 A | 10/1996 | Smesko et al. |
| 5,576,608 A | 11/1996 | Nagai et al. |
| 5,652,072 A | 7/1997 | Lamanna et al. |
| 5,670,862 A | 9/1997 | Lewyn |
| 5,691,081 A | 11/1997 | Krause et al. |
| 5,744,258 A | 4/1998 | Bai et al. |
| 5,744,264 A | 4/1998 | Barker |
| 5,776,628 A | 7/1998 | Kraft et al. |
| 5,851,696 A | 12/1998 | Saidi et al. |
| 5,882,218 A | 3/1999 | Reimers |
| 5,888,665 A | 3/1999 | Bugga et al. |
| 5,891,592 A | 4/1999 | Mao et al. |
| 5,911,947 A | 6/1999 | Mitchell |
| 5,935,724 A | 8/1999 | Spillman et al. |
| 5,935,728 A | 8/1999 | Spillman et al. |
| 5,968,681 A | 10/1999 | Miura et al. |
| 6,001,139 A | 12/1999 | Asanuma et al. |
| 6,001,507 A | 12/1999 | Ono et al. |
| 6,007,947 A | 12/1999 | Mayer |
| 6,022,643 A | 2/2000 | Lee et al. |
| 6,025,093 A | 2/2000 | Herr |
| 6,060,186 A | 5/2000 | Broussely |
| 6,067,474 A | 5/2000 | Schulman et al. |
| 6,120,938 A | 9/2000 | Atsumi et al. |
| 6,139,815 A | 10/2000 | Atsumi et al. |
| 6,165,638 A | 12/2000 | Spillman et al. |
| 6,165,646 A | 12/2000 | Takada et al. |
| 6,171,729 B1 | 1/2001 | Gan et al. |
| 6,203,947 B1 | 3/2001 | Peled et al. |
| 6,203,994 B1 | 3/2001 | Epps et al. |
| 6,207,327 B1 | 3/2001 | Takada et al. |
| 6,221,531 B1 | 4/2001 | Vaughey et al. |
| 6,228,536 B1 | 5/2001 | Wasynczuk |
| 6,258,473 B1 | 7/2001 | Spillman et al. |
| 6,265,100 B1 | 7/2001 | Saaski et al. |
| 6,274,271 B1 | 8/2001 | Koshiba et al. |
| 6,287,721 B1 | 9/2001 | Xie et al. |
| 6,316,145 B1 | 11/2001 | Kida et al. |
| 6,335,115 B1 | 1/2002 | Meissner |
| 6,352,798 B1 | 3/2002 | Lee et al. |
| 6,365,301 B1 | 4/2002 | Michot et al. |
| 6,372,384 B1 | 4/2002 | Fujimoto et al. |
| 6,379,842 B1 | 4/2002 | Mayer |
| 6,451,480 B1 | 9/2002 | Gustafson et al. |
| 6,453,198 B1 | 9/2002 | Torgerson et al. |
| 6,461,751 B1 | 10/2002 | Boehm et al. |
| 6,461,757 B1 | 10/2002 | Sasayama et al. |
| 6,475,673 B1 | 11/2002 | Yamawaki et al. |
| 6,489,062 B1 | 12/2002 | Watanabe et al. |
| 6,503,662 B1 | 1/2003 | Hamamoto et al. |
| 6,528,208 B1 | 3/2003 | Thackeray et al. |
| 6,553,263 B1 | 4/2003 | Meadows et al. |
| 6,596,439 B1 | 7/2003 | Tsukamoto et al. |
| 6,605,382 B2 | 8/2003 | Ruth et al. |
| 6,641,953 B2 | 11/2003 | Takeuchi et al. |
| 6,645,670 B2 | 11/2003 | Gan |
| 6,645,675 B1 | 11/2003 | Munshi |
| 6,670,071 B2 | 11/2003 | Takeuchi et al. |
| 6,673,493 B2 | 1/2004 | Gan et al. |
| 6,677,083 B2 | 1/2004 | Suzuki et al. |
| 6,706,445 B2 | 3/2004 | Barker et al. |
| 6,720,112 B2 | 4/2004 | Barker et al. |
| 6,730,437 B2 | 5/2004 | Leising et al. |
| 6,737,191 B2 | 5/2004 | Gan et al. |
| 6,759,168 B2 | 7/2004 | Yamasaki et al. |
| 6,761,744 B1 | 7/2004 | Tsukamoto et al. |
| 6,777,132 B2 | 8/2004 | Barker et al. |
| 6,824,920 B1 | 11/2004 | Iwamoto et al. |
| 6,841,304 B2 | 1/2005 | Michot et al. |
| 6,849,360 B2 | 2/2005 | Marple |
| 6,869,724 B2 | 3/2005 | Suzuki et al. |
| 6,905,795 B2 | 6/2005 | Jung et al. |
| 6,905,796 B2 | 6/2005 | Ishida et al. |
| 6,908,711 B2 | 6/2005 | Fauteux et al. |
| 6,942,949 B2 | 9/2005 | Besenhard et al. |
| 6,946,218 B2 | 9/2005 | Crouch et al. |
| 6,951,576 B1 | 10/2005 | Takeuchi |
| 7,018,743 B2 | 3/2006 | Guidi et al. |
| 7,029,793 B2 | 4/2006 | Nakagawa et al. |
| 7,101,642 B2 | 9/2006 | Tsukamoto et al. |
| 7,157,185 B2 | 1/2007 | Marple |
| 7,177,691 B2 | 2/2007 | Meadows et al. |
| 7,184,836 B1 | 2/2007 | Meadows et al. |
| 7,191,008 B2 | 3/2007 | Schmidt et al. |
| 7,202,000 B2 | 4/2007 | Iriyama et al. |
| 7,211,350 B2 | 5/2007 | Amatucci |
| 7,238,449 B2 | 7/2007 | Suzuki et al. |
| 7,337,010 B2 | 2/2008 | Howard et al. |
| 7,341,803 B2 | 3/2008 | Huang et al. |
| 7,459,235 B2 | 12/2008 | Choi et al. |
| 7,462,425 B2 | 12/2008 | Takami et al. |
| 7,488,553 B2 | 2/2009 | Tsukamoto et al. |
| 7,524,580 B1 | 4/2009 | Birke et al. |
| 7,541,114 B2 | 6/2009 | Ohzuku et al. |
| 7,563,541 B2 | 7/2009 | Howard et al. |
| 7,582,380 B1 | 9/2009 | Dunstan et al. |
| 7,582,387 B2 | 9/2009 | Howard et al. |
| 7,632,603 B2 | 12/2009 | Tsukamoto et al. |
| 7,662,515 B2 | 2/2010 | Inagaki et al. |
| 7,682,745 B2 | 3/2010 | Howard et al. |
| 7,740,985 B2 | 6/2010 | Howard et al. |
| 7,794,869 B2 | 9/2010 | Howard et al. |
| 7,799,470 B2 | 9/2010 | Cho et al. |
| 7,803,481 B2 | 9/2010 | Howard et al. |
| 7,807,299 B2 | 10/2010 | Howard et al. |
| 7,811,703 B2 | 10/2010 | Fujita et al. |
| 7,811,705 B2 | 10/2010 | Scott et al. |
| 7,818,068 B2 | 10/2010 | Meadows et al. |
| 7,858,236 B2 | 12/2010 | Howard et al. |
| 7,883,790 B2 | 2/2011 | Howard et al. |
| 7,927,742 B2 * | 4/2011 | Scott et al. ............... 429/231.5 |
| 2001/0008725 A1 | 7/2001 | Howard |
| 2001/0012590 A1 | 8/2001 | Ehrlich |
| 2001/0021472 A1 | 9/2001 | Barker et al. |
| 2001/0031401 A1 | 10/2001 | Yamawaki et al. |
| 2003/0025482 A1 | 2/2003 | Tsukamoto et al. |
| 2003/0104282 A1 | 6/2003 | Xing et al. |
| 2003/0124423 A1 | 7/2003 | Sasaki et al. |
| 2003/0129485 A1 | 7/2003 | Guidi et al. |
| 2003/0157410 A1 | 8/2003 | Jarvis et al. |
| 2003/0215716 A1 | 11/2003 | Suzuki et al. |
| 2004/0002005 A1 | 1/2004 | Gao et al. |
| 2004/0023117 A1 | 2/2004 | Imachi et al. |

| | | | |
|---|---|---|---|
| 2004/0062989 A1 | 4/2004 | Ueo et al. | |
| 2004/0072072 A1 | 4/2004 | Suzuki et al. | |
| 2004/0096745 A1 | 5/2004 | Shibano et al. | |
| 2004/0147971 A1 | 7/2004 | Greatbatch et al. | |
| 2004/0147972 A1 | 7/2004 | Greatbatch et al. | |
| 2004/0158296 A1 | 8/2004 | Greatbatch et al. | |
| 2004/0168307 A1 | 9/2004 | Hong | |
| 2004/0176818 A1 | 9/2004 | Wahlstrand et al. | |
| 2004/0197657 A1 | 10/2004 | Spitler et al. | |
| 2004/0209156 A1 | 10/2004 | Ren et al. | |
| 2005/0031919 A1 | 2/2005 | Ovshinsky et al. | |
| 2005/0069777 A1 | 3/2005 | Takami et al. | |
| 2005/0130043 A1 | 6/2005 | Gao et al. | |
| 2005/0147889 A1 | 7/2005 | Ohzuku et al. | |
| 2005/0164082 A1 | 7/2005 | Kishi et al. | |
| 2005/0244716 A1 | 11/2005 | Ogawa et al. | |
| 2006/0024582 A1 | 2/2006 | Li et al. | |
| 2006/0046149 A1 | 3/2006 | Yong et al. | |
| 2006/0068282 A1 | 3/2006 | Kishi et al. | |
| 2006/0090962 A1 | 5/2006 | McGehee | |
| 2006/0093871 A1 | 5/2006 | Howard et al. | |
| 2006/0093872 A1 | 5/2006 | Howard et al. | |
| 2006/0093873 A1 | 5/2006 | Howard et al. | |
| 2006/0093894 A1 | 5/2006 | Scott et al. | |
| 2006/0093913 A1 | 5/2006 | Howard et al. | |
| 2006/0093916 A1 | 5/2006 | Howard et al. | |
| 2006/0093917 A1 | 5/2006 | Howard et al. | |
| 2006/0093918 A1 | 5/2006 | Howard et al. | |
| 2006/0093921 A1 | 5/2006 | Scott et al. | |
| 2006/0093923 A1 | 5/2006 | Howard et al. | |
| 2006/0095094 A1 | 5/2006 | Howard et al. | |
| 2006/0216612 A1 | 9/2006 | Jambunathan et al. | |
| 2006/0234125 A1 | 10/2006 | Valle | |
| 2006/0251968 A1 | 11/2006 | Tsukamoto et al. | |
| 2007/0009801 A1 | 1/2007 | Inagaki et al. | |
| 2007/0059587 A1 | 3/2007 | Kishi et al. | |
| 2007/0072085 A1 | 3/2007 | Chen et al. | |
| 2007/0077496 A1 | 4/2007 | Scott et al. | |
| 2007/0111099 A1 | 5/2007 | Nanjundaswamy et al. | |
| 2007/0134556 A1 | 6/2007 | Sano et al. | |
| 2007/0162083 A1 | 7/2007 | Schmidt et al. | |
| 2007/0233195 A1 | 10/2007 | Wahlstrand et al. | |
| 2007/0239221 A1 | 10/2007 | Kast et al. | |
| 2007/0248881 A1 | 10/2007 | Scott et al. | |
| 2007/0284159 A1 | 12/2007 | Takami et al. | |
| 2008/0020278 A1 | 1/2008 | Schmidt et al. | |
| 2008/0020279 A1 | 1/2008 | Schmidt et al. | |
| 2008/0026297 A1 | 1/2008 | Chen et al. | |
| 2008/0044728 A1 | 2/2008 | Schmidt et al. | |
| 2008/0241689 A1 | 10/2008 | Takami et al. | |
| 2009/0035662 A1 | 2/2009 | Scott et al. | |
| 2009/0075166 A1 | 3/2009 | Takami et al. | |
| 2009/0241689 A1 | 10/2009 | Lorenz | |
| 2009/0274849 A1 | 11/2009 | Scott et al. | |
| 2009/0286158 A1 | 11/2009 | Howard et al. | |
| 2010/0009245 A1 | 1/2010 | Howard et al. | |
| 2010/0015528 A1 | 1/2010 | Howard et al. | |
| 2010/0076523 A1 | 3/2010 | Howard et al. | |
| 2010/0239908 A1 | 9/2010 | Howard et al. | |

FOREIGN PATENT DOCUMENTS

| | | |
|---|---|---|
| EP | 1 014 465 A1 | 6/2000 |
| EP | 1 018 773 A1 | 7/2000 |
| EP | 1 069 635 A1 | 1/2001 |
| EP | 0 567 149 B1 | 11/2001 |
| EP | 1 267 111 A1 | 12/2002 |
| EP | 1 282 180 A1 | 2/2003 |
| EP | 1 487 039 A1 | 12/2004 |
| EP | 1 722 439 A1 | 11/2006 |
| JP | 56136462 | 10/1981 |
| JP | 57011476 | 1/1982 |
| JP | 63001708 | 1/1982 |
| JP | 57152669 | 9/1982 |
| JP | 02309568 | 12/1990 |
| JP | 6275263 | 9/1994 |
| JP | 10027626 A1 | 1/1998 |
| JP | 2000-156229 A | 6/2000 |
| JP | 2000195499 | 7/2000 |
| JP | 2001-126756 A | 5/2001 |
| JP | 2001143702 A | 5/2001 |
| JP | 2001-185141 A | 7/2001 |
| JP | 2004-296256 A | 10/2004 |
| WO | WO 97/06569 A1 | 2/1997 |
| WO | WO 97/48141 A1 | 12/1997 |
| WO | WO 00/17950 A1 | 3/2000 |
| WO | WO 01/33656 A1 | 5/2001 |
| WO | WO 02/09215 A2 | 1/2002 |
| WO | WO 02/21628 A1 | 3/2002 |
| WO | WO 02/39524 A1 | 5/2002 |
| WO | WO 02/069414 A2 | 9/2002 |
| WO | WO 02/095845 A1 | 11/2002 |
| WO | WO 03/044880 A1 | 5/2003 |
| WO | WO 03/075371 A2 | 9/2003 |
| WO | WO 03/075376 A1 | 9/2003 |
| WO | WO 03/090293 A2 | 10/2003 |
| WO | WO 2004/010520 A1 | 1/2004 |
| WO | WO 2006/050022 A2 | 5/2006 |
| WO | WO 2006/050023 A2 | 5/2006 |
| WO | WO 2006/050098 A1 | 5/2006 |
| WO | WO 2006/050099 A1 | 5/2006 |
| WO | WO 2006/050100 A2 | 5/2006 |
| WO | WO 2006/050117 A1 | 5/2006 |
| WO | WO 2006/064344 A2 | 6/2006 |

OTHER PUBLICATIONS

Jansen et al, Development of a High-Power Lithium-Ion Battery, Journal of Power Sources 81-82, 1999, 4 pages.

Jarvis et al., A Li-Ion Cell Containing a Non-Lithiated Cathode, Abs. 182, IMLB 12 Meeting, 2004, 1 page.

Kavan et al., Proof of Concept—$Li_4Ti_5O_{12}$, Electrochemical and Solid State Letters, 2002, vol. 5, 1 page.

Linden, Handbook of Batteries, Second Edition, McGraw-Hill, NY, 1995, 6 pages.

Medtronic Activa® Product Family and Procedure Solution Product Specifications, 2003, 6 pages.

Medtronic Neurostimulation Systems Product Brochure, 2002 Medtronic, Inc., 6 pages.

Mikula et al., Photoelectrochemical Properties of Anodic $TiO_2$ Layers Prepared by Various Current Densities, J. Electrochemical Society, vol. 139, Dec. 1992, 5 pages.

Murphy et al., Lithium Insertion in Anatase: A New Route to the Spinel $LiTi_2O_4$, Revue De Chimie Minerale, vol. 19, 1982, 5 pages.

Murphy et al., Ternary $Li_xTiO_2$ Phases from Insertion Reactions, Solid State Ionics, vols. 9 and 10, 1983, 5 pages.

Murphy et al., Topochemical Reactions of Rutile Related Structures with Lithium, Mat. Res. Bull, 1978, vol. 13, 8 pages.

Nakahara et al., Preparation of Particulate $Li_4Ti_5O_{12}$ Having Excellent Characteristics as an Electrode Active Material for Power Storage Cells, Journal of Power Sources 117, 2003, 6 pages.

New $Li_4Ti_5O_{12}$ Anode Material of Süd-Chemie AG for Lithium Ion Batteries, Süd-Chemie EXM 1037—$Li_4Ti_5O_{12}$, Product Specification, 2 pages.

Ohzuku et al., Zero-Strain Insertion Material of $Li[Li_{1/3}Ti_{5/3}]O_4$ for Rechargeable Lithium Cells, J. Electrochem. Soc. vol. 142 #5, 1995, 5 pages.

Ohzuku et al., Lithium-Ion Batteries of $Li[Li_{1/3}Ti_{5/3}]O_4$ With Selected Positive-Electrode Materials for Long-Life Power Application, Abs. 23, IMLB 12 Meeting, 2004, 1 page.

Ohzuku et al., Why Transition Metal (Di)oxides are the Most Attractive Materials for Batteries, Solid State Ionics, vol. 69, 1994, 11 pages.

Ohzuku, Extended Abstracts from the Seventh Int'l Meeting on Li Batteries, Boston, MA, May 15-20, 1994, 3 pages.

Peramunage et al., Preparation of Micro-Sized $Li_4Ti_5O_{12}$ and Its Electrochemistry in Polyacrylonitrile Electrolye Based Lithium Cells, Technical Papers, Electrochemical Science and Technology, J. Electrochem Soc., vol. 145, No. 8, Aug. 1998, 8 pages.

Poizot et al., Nano-sized transition-metal oxides as negative-electrode materials for lithium-ion batteries, Nature, vol. 407, 2000, 5 pages.

Sasaki et al., Layered Hydrous Titanium Dioxide: Potassium Ion Exchange and Structural Characterization, Inorganic Chemistry, 1985, vol. 24, No. 14, 4 pages.

Sawai et al., Factors Affecting Rate Capability of a Lithium-ion Battery with Li[Li1/3Ti5/3]O4 and LiCo1/2Ni1/2O2, Abs. 75, 2004, 3 pages.
Scrosati, Low Voltage Lithium-Ion Cells, Advances in Lithium-Ion Batteries, Kluwer Academic/Plenum Publishers, 2002, 21 pages.
Singhal et al., Nanostructured Electrodes for Next Generation Rechargeable Electrochemical Devices, Journal of Power Sources, 129, 2004, 7 pages.
Sun et al., Using a Boron Based Anion Receptor Additive to Improve the Thermal Stability of LiPF6 Based Electrolyte for Lithium Batteries, (ECS) Electrochemical and Solid-State Letters, 2002, 4 pages.
Sun et al., The Compatibility of a Boron Based Anion Receptor with the Carbon Anode in Lithium-Ion Batteries, Electrochemical and Solid-State Letters 6, 2003, 4 pages.
Trifonova et al., Sn-Sb and Sn Bi Alloys as Anode Materials for Lithium-Ion Batteries, Ionics, vol. 8, 2002, 9 pages.
Wang et al., Novel Electrolytes for Nanocrystalline Li4Ti5O12 Based High Power Lithium Ion Batteries, 1 page.
Wang et al., Li Insertion and Ion Exchange Reactions in the Ionic Conducting TI2(M,Ti)8O16 Phases with Hollandite-Type Structure, J. Electrochem Soc., vol. 138, No. 1, Jan. 1991, 7 pages.
Winter et al., Insertion Electrode Materials for Rechargeable Lithium Batteries, Advanced Materials, vol. 10, 1998, 41 pages.
Winter et al., Electrochemical Lithiation of Tin and Tin Based Intermetallics and Composites, Electrochimica Acta, vol. 45, 1999, 10 pages.
XKnife™ RT, Integra Radionics, www.radionics.com, Jul. 10, 2006, 2 pages.
Zaghib et al., Electrochemical Study of Li4Ti5O12 As Negative Electrode for Li-Ion Polymer Rechargeable Batteries, Journal of Power Sources, 81-82, 1999, 6 pages.
International Search Report for PCT/US2005/038762, mail date Oct. 2, 2006, 2 pages.
International Search Report for PCT/US2005/038761, mail date Oct. 4, 2006, 2 pages.
International Search Report for PCT/US2005/038942, mail date Mar. 2, 2006, 3 pages.
International Search Report for PCT/US2005/038943, mail date Mar. 16, 2006, 3 pages.
International Search Report for PCT/US2005/038944, mail date Mar. 31, 2006, 3 pages.
International Search Report for PCT/US2005/038970, mail date Oct. 25, 2006, 3 pages.
International Search Report and Written Opinion for Application No. PCT/US2008/066801, mail date Oct. 29, 2008, 10 pages.
International Search Report and Written Opinion for Application No. PCT/US2008/066803, mail date Oct. 7, 2008, 12 pages.
International Search Report and Written Opinion for Application No. PCT/US2008/066809, mail date Oct. 29, 2008, 8 pages.
English Translation of Third Office Action for Chinese Application No. 200580036854.4, dated Jul. 30, 2010, 9 pages.
English Translation of Fourth Office Action for Chinese Application No. 200580036854.4, dated Feb. 11, 2011, 9 pages.
Preliminary Amendment for U.S. Appl. No. 12/240,652, filed Oct. 7, 2008, 3 pages.
Non-Final Office Action for U.S. Appl. No. 12/240,652, dated Jun. 2, 2009, 6 pages.
Amendment and Reply for U.S. Appl. No. 12/240,652, filed Sep. 2, 2009, 13 pages.
Final Office Action for U.S. Appl. No. 12/240,652, dated Nov. 19, 2009, 8 pages.
RCE and Amendment and Reply for U.S. Appl. No. 12/240,652, filed Jan. 21, 2010, 17 pages.
Non-Final Office Action for U.S. Appl. No. 12/240,652, dated Apr. 21, 2010, 10 pages.
Amendment and Reply for U.S. Appl. No. 12/240,652, filed Jul. 21, 2010, 17 pages.
Final Office Action for U.S. Appl. No. 12/240,652, dated Aug. 25, 2010, 7 pages.
Amendment and Reply and Terminal Disclaimer for U.S. Appl. No. 12/240,652, filed Sep. 23, 2010, 13 pages.
Advisory Action for U.S. Appl. No. 12/240,652, dated Sep. 30, 2010, 3 pages.
Amendment and Reply for U.S. Appl. No. 12/240,652, filed Dec. 14, 2010, 12 pages.
Notice of Allowance for U.S. Appl. No. 12/240,652, dated Dec. 28, 2010, 4 pages.
Non-Final Office Action for U.S. Appl. No. 10/979,040, dated Apr. 2, 2008, 8 pages.
U.S. Appl. No. 13/081,050, filed Apr. 6, 2011, Howard et al.
Ariyoshi et al., Three-Volt Lithium-Ion Battery with Li[Ni1/2Mn3/2]O4 and the Zero-Strain Insertion Material of Li[Li1/3Ti5/3]O4, Journal of Power Sources 119-121, 2003, 5 pages.
Battery Materials, Ceramic Anode Material for 2.4 V Lithium-Ion Batteries, Oct. 25, 2004, 1 page.
Belharouak et al., On the Safety of the Li4Ti5O12/LiMn2O4 Lithium-Ion Battery System, Journal of The Electrochemical Society, vol. 154, 2007, 5 pages.
Brohan et al., Properties Physiques Des Bronzes MxTiO2(B), Solid State Ionics, vols. 9 and 10, 1983, 6 pages.
Cava et al., The Crystal Structures of the Lithium-Inserted Metal Oxides Li0.5TiO2 Anatase, LiTi2O4 Spinel, and Li2Ti2O4, Journal of Solid State Chemistry, vol. 53, 1984, 12 pages.
Christensen et al., Optimization of Lithium Titanate Electrodes for High-Power Cells, (ECS) Journal of The Electrochemical Society, 2006, vol. 153, 6 pages.
Colbow et al., Structure and Electrochemistry of the Spinel Oxides LiTi2O4 and Li4/3Ti5/3O4, Journal of Power Sources 26, 1989, 6 pages.
Dahn et al., Combinatorial Study of Sn1-xCox (0 < x < 0.6) and [Sn0.55Co0.45]1-yCy (0 < y < 0.5) Alloy Negative Electrode Materials for Li-Ion Batteries, Journal of Electrochemical Society, vol. 153, 2006, 5 pages.
Fauteux et al., Rechargeable lithium battery anodes: alternatives to metallic lithium, Journal of Applied Electrochemistry, vol. 23, 1993, 10 pages.
Ferg et al., Spinel Anodes for Lithium-Ion Batteries, J. Electrochem. Soc. 141, Nov. 1994, 4 pages.
FMC Lithium, CAS No. 74389-93-2, Stabilized Lithium Metal Powder Product Specification, 2001, FMC Corporation, 2 pages.
Guerfi et al., Nano Electronically Conductive Titanium-Spinel as Lithium Ion Storage Negative Electrode, Journal of Power Sources, 126, 2004, 6 pages.
Reply and Amendment and Declaration Under 1.131 for U.S. Appl. No. 10/979,040, filed Jul. 16, 2008, 33 pages.
Final Office Action for U.S. Appl. No. 10/979,040, dated Sep. 19, 2008, 10 pages.
RCE and Reply and Amendment for U.S. Appl. No. 10/979,040, filed Dec. 11, 2008, 16 pages.
Non-Final Office Action for U.S. Appl. No. 10/979,040, dated Jan. 12, 2009, 10 pages.
Reply and Amendment for U.S. Appl. No. 10/979,040, filed Mar. 24, 2009, 12 pages.
Final Office Action for U.S. Appl. No. 10/979,040, dated Jun. 16, 2009, 10 pages.
Reply and Amendment for U.S. Appl. No. 10/979,040, filed Aug. 17, 2009, 13 pages.
Advisory Action for U.S. Appl. No. 10/979,040, dated Aug. 24, 2009, 3 pages.
RCE for U.S. Appl. No. 10/979,040, filed Sep. 11, 2009, 3 pages.
Non-Final Office Action for U.S. Appl. No. 10/979,040, dated Sep. 30, 2009, 7 pages.
Reply and Amendment for U.S. Appl. No. 10/979,040, filed Dec. 16, 2009, 10 pages.
Final Office Action for U.S. Appl. No. 10/979,040, dated Feb. 25, 2010, 8 pages.
Reply and Amendment for U.S. Appl. No. 10/979,040, filed Apr. 22, 2010, 12 pages.
Advisory Action for U.S. Appl. No. 10/979,040, dated Apr. 27, 2010, 3 pages.
RCE for U.S. Appl. No. 10/979,040, filed May 7, 2010, 4 pages.
Notice of Allowance for U.S. Appl. No. 10/979,040, dated Jun. 11, 2010, 13 pages.
Non-Final Office Action for U.S. Appl. No. 10/978,712, dated Apr. 10, 2008, 12 pages.

Reply and Amendment and Declaration Under 1.131 for U.S. Appl. No. 10/978,712, filed Jul. 16, 2008, 36 pages.
Final Office Action for U.S. Appl. No. 10/978,712, dated Oct. 9, 2008, 7 pages.
RCE, Reply and Amendment, and Terminal Disclaimers for U.S. Appl. No. 10/978,712, filed Dec. 8, 2008, 20 pages.
Non-Final Office Action for U.S. Appl. No. 10/978,712, dated Jan. 5, 2009, 16 pages.
Reply and Amendment for U.S. Appl. No. 10/978,712, filed Mar. 24, 2009, 16 pages.
Final Office Action for U.S. Appl. No. 10/978,712, dated Jun. 17, 2009, 11 pages.
Reply and Amendment for U.S. Appl. No. 10/978,712, filed Aug. 14, 2009, 14 pages.
Advisory Action for U.S. Appl. No. 10/978,712, dated Aug. 27, 2009, 3 pages.
RCE, Reply and Amendment, and Terminal Disclaimer for U.S. Appl. No. 10/978,712, filed Oct. 19, 2009, 22 pages.
Terminal Disclaimer for U.S. Appl. No. 10/978,712, filed Nov. 11, 2009, 4 pages.
Notice of Allowance for U.S. Appl. No. 10/978,712, dated Dec. 1, 2009, 14 pages.
Non-Final Office Action for U.S. Appl. No. 11/260,853, dated Mar. 5, 2009, 13 pages.
Amendment and Reply for U.S. Appl. No. 11/260,853, filed Jun. 4, 2009, 14 pages.
Notice of Allowance for U.S. Appl. No. 11/260,853, dated Aug. 5, 2009, 7 pages.
Restriction Requirement for U.S. Appl. No. 12/454,718, dated Sep. 22, 2009, 9 pages.
Restriction Response for U.S. Appl. No. 12/454,718, filed Oct. 22, 2009, 11 pages.
Non-Final Office Action for U.S. Appl. No. 12/454,718, dated Dec. 1, 2009, 7 pages.
Reply and Amendment for U.S. Appl. No. 12/454,718, filed Mar. 1, 2010, 13 pages.
Non-Final Office Action for U.S. Appl. No. 12/454,718, dated Apr. 21, 2010, 6 pages.
Reply and Amendment for U.S. Appl. No. 12/454,718, filed Jul. 21, 2010, 10 pages.
Final Office Action for U.S. Appl. No. 12/454,718, dated Aug. 25, 2010, 8 pages.
Reply and Amendment and Terminal Disclaimer for U.S. Appl. No. 12/454,718, filed Sep. 23, 2010, 12 pages.
Notice of Allowance for U.S. Appl. No. 12/454,718, dated Sep. 30, 2010, 6 pages.
Restriction Requirement for U.S. Appl. No. 11/777,599, dated Dec. 8, 2010, 8 pages.
Restriction Response for U.S. Appl. No. 11/777,599, filed Jan. 10, 2011, 9 pages.
Non-Final Office Action for U.S. Appl. No. 11/777,599, dated Feb. 1, 2011, 20 pages.
Amendment and Reply for U.S. Appl. No. 11/777,599, filed May 2, 2011, 19 pages.
Non-Final Office Action for U.S. Appl. No. 11/777,599, dated Jul. 8, 2011, 17 pages.
Restriction Requirement for U.S. Appl. No. 11/777,609, dated Dec. 13, 2010, 8 pages.
Restriction Response for U.S. Appl. No. 11/777,609, filed Jan. 13, 2011, 9 pages.
Non-Final Office Action for U.S. Appl. No. 11/777,609, dated Feb. 2, 2011, 18 pages.
Amendment and Reply for U.S. Appl. No. 11/777,609, filed May 2, 2011, 16 pages.
Final Office Action for U.S. Appl. No. 11/777,609, dated Jul. 7, 2011, 16 pages.
Restriction Requirement for U.S. Appl. No. 11/777,628, dated Dec. 28, 2010, 8 pages.
Restriction Response for U.S. Appl. No. 11/777,628, filed Jan. 13, 2011, 10 pages.
Non-Final Office Action for U.S. Appl. No. 11/777,628, dated Feb. 9, 2011, 8 pages.
Amendment and Reply for U.S. Appl. No. 11/777,628, filed May 9, 2011, 14 pages.
Non-Final Office Action for U.S. Appl. No. 11/777,628, dated Jun. 13, 2011, 8 pages.
Amendment and Reply for U.S. Appl. No. 11/777,599, mail date Nov. 9, 2011, 11 pages.
Final Office Action for U.S. Appl. No. 11/777,599, mail date Dec. 23, 2011, 19 pages.
Response for U.S. Appl. No. 11/777,609, mail date Sep. 7, 2011, 11 pages.
Advisory Action for U.S. Appl. No. 11/777,609, mail date Sep. 20, 2011, 3 pages.
Request for Continued Examination (RCE) and Amendment and Reply for U.S. Appl. No. 11/777,609, mail date Oct. 7, 2011, 15 pages.
Non-Final Office Action for U.S. Appl. No. 11/777,609, mail date Oct. 27, 2011, 17 pages.
Amendment and Reply for U.S. Appl. No. 11/777,628, mail date Sep. 13, 2011, 18 pages.
Notice of Allowance for U.S. Appl. No. 11/777,628, mail date Oct. 14, 2011, 5 pages.
Restriction Requirement for U.S. Appl. No. 12/112,979, mail date Oct. 6, 2011, 8 pages.
Restriction Response for U.S. Appl. No. 12/112,979, mail date Nov. 4, 2011, 8 pages.
Request for Continued Examination (RCE), Amendment and Reply, and Declaration Under 1.132 for U.S. Appl. No. 11/777,609, mail date Jul. 24, 2012, 103 pages.
Non-Final Office Action for U.S. Appl. No. 12/112,979, mail date Jun. 5, 2012, 10 pages.
Non-Final Office Action for U.S. Appl. No. 11/777,599, mail date Oct. 11, 2012, 23 pages.
Non-Final Office Action for U.S. Appl. No. 11/777,609, mail date Sep. 28, 2012, 18 pages.
Amendment and Reply for U.S. Appl. No. 12/112,979, mail date Oct. 5, 2012, 9 pages.

* cited by examiner

NEGATIVE-LIMITED LITHIUM-ION BATTERY

CROSS-REFERENCE TO RELATED APPLICATIONS

The present application is a Continuation of U.S. patent application Ser. No. 12/240,652, filed Sep. 29, 2008 (now U.S. Pat. No. 7,927,742), which is a Continuation-in-Part of both U.S. patent application Ser. No. 10/979,040, filed Oct. 29, 2004 (now U.S. Pat. No. 7,811,705) and U.S. patent application Ser. No. 12/112,979, filed Apr. 30, 2008. The entire disclosures of U.S. patent application Ser. No. 12/240,652 (now U.S. Pat. No. 7,927,742), U.S. patent application Ser. No. 10/979,040 (now U.S. Pat. No. 7,811,705), and U.S. patent application Ser. No. 12/112,979 are incorporated by reference herein.

BACKGROUND

The present application relates generally to the field of rechargeable lithium-ion batteries or cells.

Lithium-ion batteries or cells (i.e., rechargeable or "secondary" batteries) include one or more positive electrodes, one or more negative electrodes, and an electrolyte provided within a case or housing. Separators made from a porous polymer or other suitable material may also be provided intermediate or between the positive and negative electrodes to prevent direct contact between adjacent electrodes. The positive electrode includes a current collector having an active material provided thereon, and the negative electrode includes a current collector having an active material provided thereon. The active materials for the positive and negative electrodes may be provided on one or both sides of the current collectors.

FIG. 1 shows a schematic representation of a portion of a lithium-ion battery 10 such as that described above. The battery 10 includes a positive electrode 20 that includes a positive current collector 22 and a positive active material 24, a negative electrode 30 that includes a negative current collector 32 and a negative active material 34, an electrolyte material 40, and a separator (e.g., a polymeric microporous separator, not shown) provided intermediate or between the positive electrode 20 and the negative electrode 30. The electrodes 20, 30 may be provided as relatively flat or planar plates or may be wrapped or wound in a spiral or other configuration (e.g., an oval configuration). The electrode may also be provided in a folded configuration.

During charging and discharging of the battery 10, lithium ions move between the positive electrode 20 and the negative electrode 30. For example, when the battery 10 is discharged, lithium ions flow from the negative electrode 30 to the positive electrode 20. In contrast, when the battery 10 is charged, lithium ions flow from the positive electrode 20 to the negative electrode 30.

Once assembly of the battery is complete, an initial charging operation (referred to as a "formation process") may be performed. During this process, a stable solid-electrolyte-inter-phase (SEI) layer is formed at the negative electrode and also possibly at the positive electrode. These SEI layers act to passivate the electrode-electrolyte interfaces as well as to prevent side-reactions thereafter.

One issue associated with conventional lithium-ion batteries relates to the ability of the batteries to withstand repeated charge cycling that involves discharges to near-zero-volt conditions (so-called "deep discharge" conditions). This deep discharge cycling may decrease the attainable full charge capacity of the batteries, which is known in the art as capacity fade. For example, a battery that initially is charged to 2.8 volts (V) may experience capacity fade with repeated deep discharge cycling such that after 150 cycles, the full charge capacity of the battery is much less than the initial capacity.

One consequence of capacity fade is that the batteries require increasingly frequent recharging as the capacity fade progresses, which may be relatively inconvenient for the user of the batteries. For example, certain implantable medical devices may utilize rechargeable batteries as a power source, and more frequent charging may be inconvenient for a patient.

Rechargeable lithium-ion batteries are conventionally designed so that the capacity of the active material provided on the negative electrode is equal to or greater than the capacity of the active material provided on the positive electrode. One reason for this design rule is the desire to avoid lithium plating at the negative electrode. In lithium plating, lithium ions that would otherwise be responsible for shuttling between the electrodes during charging and discharging of the battery are deposited on the negative electrode as lithium metal and, due to reasons such as isolation or passivation of the lithium metal, thereafter do not participate in the charging and discharge function. This lithium plating leads to a decrease in overall battery capacity.

It would be advantageous to provide a rechargeable lithium-ion battery that utilizes materials that provide increased resistance to lithium plating, which may eliminate the need to adhere to design rules such as those requiring capacity balancing of the electrodes. This in turn may provide the opportunity to reduce the amount of certain materials used in batteries. It would also be advantageous to provide a rechargeable battery (e.g., a lithium-ion battery) with increased resistance to capacity fade.

SUMMARY

An exemplary embodiment relates to a rechargeable lithium-ion battery that includes a positive electrode having a first capacity and a negative electrode having a second capacity that is less than the first capacity such that the battery has a negative-limited design. The negative electrode comprises a lithium titanate active material. The battery also includes a liquid electrolyte comprising a lithium salt dissolved in at least one non-aqueous solvent and a porous polymeric separator located between the positive electrode and negative electrode, wherein the separator is configured to allow lithium ions to flow through the separator.

Another exemplary embodiment relates to a rechargeable lithium-ion battery that includes a positive electrode and a negative electrode comprising a lithium titanate active material that cycles lithium at a potential of greater than 0.2 volts versus a lithium reference electrode. The battery also includes a liquid electrolyte comprising ethylene carbonate and free of molten salt and a porous polymeric separator. The positive electrode has a first capacity and the negative electrode has a second capacity, the second capacity being less than the first capacity such that the battery is negative-limited, whereby the battery exhibits improved resistance to capacity fade after repeated cycling as compared to batteries having balanced electrode capacities.

Another exemplary embodiment relates to a rechargeable lithium-ion battery that includes a positive electrode and a negative electrode comprising a lithium titanate active material. The rechargeable lithium-ion battery also includes a liquid electrolyte that is free of molten salt and a porous polymeric separator. The rechargeable lithium-ion battery has a negative-limited cell balance such that the positive electrode has greater capacity than the negative electrode and wherein the capacity fade rate of the negative electrode is less than that of the positive electrode.

DETAILED DESCRIPTION

According to an exemplary embodiment, a rechargeable lithium-ion battery or cell includes a positive electrode having an active material provided thereon and a negative electrode having an active material provided thereon. The active material provided on the negative electrode includes an active material that cycles lithium at greater than 0.2 volts versus a lithium reference electrode. One example of such a material is lithium titanate (e.g., $Li_4Ti_5O_{12}$). An electrolyte is also provided in the battery which does not include a molten salt (e.g., ionic liquid) component. The capacity of the negative electrode is less than the capacity of the positive electrode such that the battery is negative-limited. The negative-limited battery exhibits improved resistance to capacity fade as compared to batteries that are balanced (i.e., those having capacity ratios between the negative and positive electrodes of 1.0).

Figure 1:
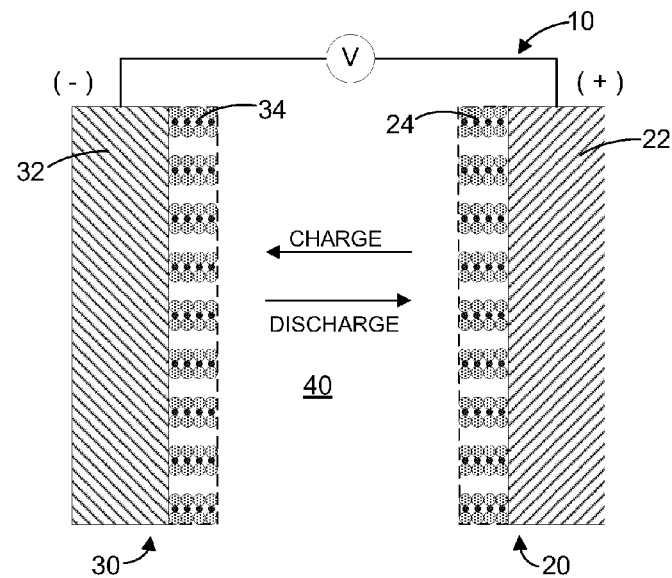
FIG. 1 is a cross-sectional view of a portion of a lithium-ion battery according to an exemplary embodiment.
Figure 2:
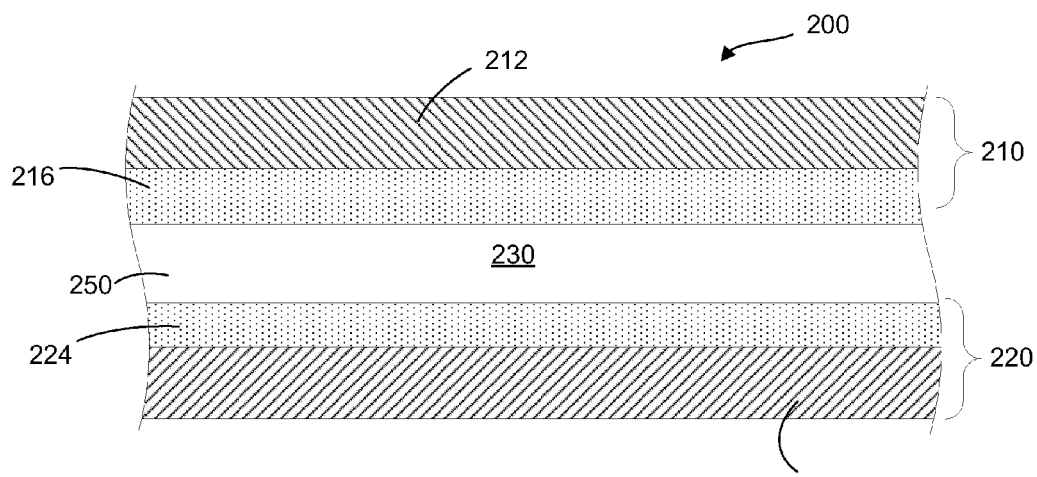
FIG. 2 is a schematic cross-sectional view of a portion of a lithium-ion battery according to an exemplary embodiment.

FIG. 2 is a schematic cross-sectional view of a portion of a battery or cell 200 according to an exemplary embodiment that includes at least one positive electrode 210 and at least one negative electrode 220. The size, shape, and configuration of the battery may be selected based on the desired application or other considerations. For example, the electrodes may be flat plate electrodes, wound electrodes (e.g., in a jellyroll, folded, or other configuration), or folded electrodes (e.g., Z-fold electrodes). According to other exemplary embodiments, the battery may be a button cell battery, a thin film solid state battery, or another type of lithium-ion battery.

According to an exemplary embodiment, the battery 200 has a rating of between approximately 1 and 1000 milliampere hours (mAh). According to another exemplary embodiment, the battery has a rating of between approximately 100 and 400 mAh. According to another exemplary embodiment, the battery is an approximately 300 mAh battery. According to another exemplary embodiment, the battery is an approximately 75 mAh battery. According to another exemplary embodiment, the battery is an approximately 10 mAh battery.

The battery case or housing (not shown) is formed of a metal or metal alloy such as aluminum or alloys thereof, titanium or alloys thereof, stainless steel, or other suitable materials. According to another exemplary embodiment, the battery case may be made of a plastic material or a plastic-foil laminate material (e.g., an aluminum foil provided intermediate a polyolefin layer and a nylon or polyester layer).

An electrolyte is provided intermediate or between the positive and negative electrodes to provide a medium through which lithium ions may travel. According to an exemplary embodiment, the electrolyte may be a liquid (e.g., a lithium salt dissolved in one or more non-aqueous solvents). According to an exemplary embodiment, the electrolyte may be a mixture of ethylene carbonate (EC), ethylmethyl carbonate (EMC) and a 1.0 M salt of $LiPF_6$. According to another exemplary embodiment, an electrolyte may be used that uses constituents that may commonly be used in lithium batteries (e.g., propylene carbonate, dimethyl carbonate, vinylene carbonate, lithium bis-oxalatoborate salt (sometimes referred to as LiBOB), etc.). It should be noted that according to an exemplary embodiment, the electrolyte does not include a molten salt.

Various other electrolytes may be used according to other exemplary embodiments. According to an exemplary embodiment, the electrolyte may be a lithium salt dissolved in a polymeric material such as poly(ethylene oxide) or silicone. According to another exemplary embodiment, the electrolyte may be an ionic liquid such as N-methyl-N-alkylpyrrolidinium bis(trifluoromethanesulfonyl)imide salts. According to another exemplary embodiment, the electrolyte may be a 3:7 mixture of ethylene carbonate to ethylmethyl carbonate (EC:EMC) in a 1.0 M salt of $LiPF_6$. According to another exemplary embodiment, the electrolyte may include a polypropylene carbonate solvent and a lithium bis-oxalatoborate salt. According to other exemplary embodiments, the electrolyte may comprise one or more of a PVDF copolymer, a PVDF-polyimide material, and organosilicon polymer, a thermal polymerization gel, a radiation cured acrylate, a particulate with polymer gel, an inorganic gel polymer electrolyte, an inorganic gel-polymer electrolyte, a PVDF gel, polyethylene oxide (PEO), a glass ceramic electrolyte, phosphate glasses, lithium conducting glasses, and lithium conducting ceramics, among others.

A separator 250 is provided intermediate or between the positive electrode 210 and the negative electrode 220. According to an exemplary embodiment, the separator 250 is a polymeric material such as a polypropylene/polyethelene copolymer or another polyolefin multilayer laminate that includes micropores formed therein to allow electrolyte and lithium ions to flow from one side of the separator to the other. The thickness of the separator 250 is between approximately 10 micrometers ($\mu$m) and 50 $\mu$m according to an exemplary embodiment. According to a particular exemplary embodiment, the thickness of the separator is approximately 25 $\mu$m, and the average pore size of the separator is between approximately 0.02 $\mu$m and 0.1 $\mu$m.

The positive electrode 210 includes a current collector 212 made of a conductive material such as a metal. According to an exemplary embodiment, the current collector 212 comprises aluminum or an aluminum alloy.

According to an exemplary embodiment, the thickness of the current collector 212 is between approximately 5 $\mu$m and 75 $\mu$m. According to a particular exemplary embodiment, the thickness of the current collector 212 is approximately 20 $\mu$m. It should also be noted that while the positive current collector 212 has been illustrated and described as being a thin foil material, the positive current collector may have any of a variety of other configurations according to various exemplary embodiments. For example, the positive current collector may be a grid such as a mesh grid, an expanded metal grid, a photochemically etched grid, or the like.

The current collector 212 has a layer of active material 216 provided thereon (e.g., coated on the current collector). While FIG. 2 shows that the active material 216 is provided on only one side of the current collector 212, it should be understood that a layer of active material similar or identical to that shown as active material 216 may be provided or coated on both sides of the current collector 212.

According to an exemplary embodiment, the active material 216 is a material or compound that includes lithium. The lithium included in the active material 216 may be doped and undoped during discharging and charging of the battery, respectively. According to an exemplary embodiment, the active material 216 is lithium cobalt oxide ($LiCoO_2$). According to other exemplary embodiments, the active material may be provided as one or more additional materials. For example, the active material may be $LiMn_2O_4$ or a material having the formula $LiCO_xNi_{(1-x)}O_2$, where x is between approximately 0.05 and 0.8. According to another exemplary embodiment, the active material is a material of the form $LiNi_xCo_yMn_{(1-x-y)}O_2$ (e.g., $LiNi_{1/3}Co_{1/3}Mn_{1/3}O_2$ or $LiNi_{0.8}Co_{0.1}Mn_{0.1}O_2$). According to another exemplary embodiment, the active material 216 is a metal-doped variety of one of the aforementioned materials, such as a material of the form $LiM_xCo_yNi_{(1-x-y)}O_2$, where M is aluminum or titanium and x is between approximately 0.05 and 0.3 and y is between approximately 0.1 and 0.3.

For certain applications, it may be desirable to provide a battery having a cell voltage of greater than approximately 3 volts. In such cases, a higher-voltage active material may be utilized on the positive current collector, such as a material in the form $Li_{2-x}Co_yFe_zMn_{4-(y+z)}O_8$ (e.g., $Li_2Co_{0.4}Fe_{0.4}Mn_{3.2}O_8$). It is believed that such an active material may charge up to 5.2 volts versus a lithium reference electrode, making it possible to obtain an overall cell voltage of up to approximately 3.7 volts. Other relatively high-voltage active materials that may be used for the positive electrode include $LiCoPO_4$; $LiNiPO_4$; $Li_2CoPO_4F$; $Li[Ni_{0.2}Li_{0.2}Mn_{0.6}]O_2$; and $LiCo_xMn_{2-x}O_4$ (e.g., $LiCo_{0.3}Mn_{1.7}O_4$). Other high voltage active materials that may be used could be based on the compositions $LiM_xMn_{2-x}O_4$ (where M=Ni, Fe with 0<x<0.5) or a material having the formula $Li_{1-x/3}M_{0.5-x/2}Mn_{1.5+x/6}O_4$ where x=0 to 0.5 and M=Ni, Fe).

According to various other exemplary embodiments, the active material may include a material such as a material of the form $Li_{1-x}MO_2$ where M is a metal (e.g., $LiCoO_2$, $LiNiO_2$, and $LiMnO_2$), a material of the form $Li_{1-w}(M'_xM''_y)O_2$ where M' and M'' are different metals (e.g., $Li(Cr_xMn_{1-x})O_2$, $Li(Al_xMn_{1-x})O_2$, $Li(Co_xM_{1-x})O_2$ where M is a metal, $Li(Co_xNi_{1-x})O_2$, and $Li(Co_xFe_{1-x})O_2$)), a material of the form $Li_{1-w}(Mn_xNi_yCo_z)O_2$ (e.g., $Li(Mn_{1/3}Ni_{1/3}Co_{1/3})O_2$, $Li(Mn_{1/3}Ni_{1/3}Co_{1/3-x}Mg_x)O_2$, $Li(Mn_{0.4}Ni_{0.4}Co_{0.2})O_2$, and $Li(Mn_{0.1}Ni_{0.1}Co_{0.8})O_2$), a material of the form $Li_{1-w}(Mn_xNi_xCo_{1-2x})O_2$, a material of the form $Li_{1-w}(Mn_xNi_yCo_zAl_w)O_2$, a material of the form $Li_{1-w}(Ni_xCo_yAl_z)O_2$ (e.g., $Li(Ni_{0.8}Co_{0.15}Al_{0.05})O_2$), a material of the form $Li_{1-w}(Ni_xCo_yM_z)O_2$ where M is a metal, a material of the form $Li_{1-w}(Ni_xMn_yM_z)O_2$ where M is a metal, a material of the form $Li(Ni_{x-y}Mn_yCr_{2-x})O_4$, $LiMn_2O_4$, a material of the form $LiM'M''_2O_4$ where M' and M'' are different metals (e.g., $LiMn_{2-y-z}Ni_yO_4$, $Li_zO_4$, $LiNiCuO_4$, $LiMn_{1-x}Al_xO_4$, $LiNi_{0.5}Ti_{0.5}O_4$, and $Li_{1.05}Al_{0.1}Mn_{1.85}O_{4-z}F_z$), $Li_2MnO_3$, a material of the form $Li_xV_yO_z$ (e.g., $LiV_3O_8$, $LiV_2O_5$, and $LiV_6O_{13}$), a material of the form $LiMPO_4$ where M is a metal or $LiM'_xM''_{1-x}PO_4$ where M' and M'' are different metals (e.g., $LiFePO_4$, $LiFe_xM_{1-x}PO_4$ where M is a metal, $LiVOPO_4$, and $Li_3V_2(PO_4)_3$, and $LiMPO_{4X}$ where M is a metal such as iron or vanadium and X is a halogen such as fluorine, and combinations thereof.

A binder material may also be utilized in conjunction with the layer of active material 216 to bond or hold the various electrode components together. For example, according to an exemplary embodiment, the layer of active material may include a conductive additive such as carbon black and a binder such as polyvinylidine fluoride (PVDF) or an elastomeric polymer.

According to an exemplary embodiment, the thickness of the layer of active material 216 is between approximately 0.1 $\mu$m and 3 mm. According to another exemplary embodiment, the thickness of the layer of active material 216 is between approximately 25 $\mu$m and 300 $\mu$m. According to a particular exemplary embodiment, the thickness of the layer of active material 216 is approximately 75 $\mu$m.

The negative electrode 220 includes a current collector 222 that is made of a conductive material such as a metal. According to an exemplary embodiment, the current collector 222 is aluminum or an aluminum alloy. One advantageous feature of utilizing an aluminum or aluminum alloy current collector is that such a material is relatively inexpensive and may be relatively easily formed into a current collector. Other advantageous features of using aluminum or an aluminum alloy includes the fact that such materials may have a relatively low density, are relatively highly conductive, are readily weldable, and are generally commercially available. According to another exemplary embodiment, the current collector 222 is titanium or a titanium alloy. According to another exemplary embodiment, the current collector 222 is silver or a silver alloy.

While the negative current collector 222 has been illustrated and described as being a thin foil material, the negative current collector may have any of a variety of other configurations according to various exemplary embodiments. For example, the positive current collector may be a grid such as a mesh grid, an expanded metal grid, a photochemically etched grid, a metallized polymer film, or the like.

According to an exemplary embodiment, the thickness of the current collector 222 is between approximately 100 nm and 100 $\mu$m. According to another exemplary embodiment, the thickness of the current collector 222 is between approximately 5 $\mu$m and 25 $\mu$m. According to a particular exemplary embodiment, the thickness of the current collector 222 is approximately 10 $\mu$m.

The negative current collector 222 has an active material 224 provided thereon. While FIG. 2 shows that the active material 224 is provided on only one side of the current collector 222, it should be understood that a layer of active material similar or identical to that shown may be provided or coated on both sides of the current collector 222.

According to an exemplary embodiment, the negative active material is selected such that it has an average potential that is greater or equal to approximately 0.2 V versus Li/Li+ (e.g., according to one particular exemplary embodiment, the negative active material has an average potential that is greater or equal to approximately 0.3 V versus Li/Li+; according to a particularly preferred embodiment, the negative active material is a titanate material having an average potential that is greater or equal to approximately 1.5 V versus Li/Li+). The inventors have unexpectedly discovered that the use of negative electrode materials that possess a relatively high average potential versus Li/Li+ reduces the likelihood of lithium plating. According to one exemplary embodiment, such a negative active material is used in conjunction with a positive active material that has an average potential of greater than approximately 3 V versus Li/Li+ (e.g., LiCoO$_2$).

According to an exemplary embodiment, the negative active material 224 is a lithium titanate material such as Li$_4$Ti$_5$O$_{12}$ (sometimes referred to as Li$_{1+x}$[Li$_{1/3}$Ti$_{5/3}$]O$_4$, with $0 \leq x<1$). Other lithium titanate materials which may be suitable for use as the negative active material may include one or more of the following lithium titanate spinel materials: H$_x$Li$_{y-x}$TiO$_x$O$_4$, H$_x$Li$_{y-x}$TiO$_x$O$_4$, Li$_4$M$_x$Ti$_{5-x}$O$_{12}$, Li$_x$Ti$_y$O$_4$, Li$_x$Ti$_y$O$_4$, Li$_4$[Ti$_{1.67}$Li$_{0.33-y}$M$_y$]O$_4$, Li$_2$TiO$_3$, Li$_4$Ti$_{4.75}$V$_{0.25}$O$_{12}$, Li$_4$Ti$_{4.75}$Fe$_{0.25}$O$_{11.88}$, Li$_4$Ti$_{4.5}$Mn$_{0.5}$O$_{12}$, and LiM'M"XO$_4$ (where M' is a metal such as nickel, cobalt, iron, manganese, vanadium, copper, chromium, molybdenum, niobium, or combinations thereof, M" is an optional three valent non-transition metal, and X is zirconium, titanium, or a combination of these two). Note that such lithium titanate spinel materials may be used in any state of lithiation (e.g., Li$_{4+x}$Ti$_5$O$_{12}$, where $0 \leq x \leq 3$).

According to an exemplary embodiment, the lithium titanate may be provided such that at least five percent is in the form of lithium titanate nanoparticles (e.g., having a particle size of less than approximately 500 nanometers). The use of such nonoparticles is intended to provide greater surface area for doping and undoping of lithium ions.

According to other exemplary embodiments, a lithium vanadate (e.g., Li$_{1.1}$V$_{0.9}$O$_2$) material may be used as the negative active material. Another exemplary embodiment may have the compound TiO$_2$ (B) with a charge discharge voltage of 2.0-1.0 V versus a lithium reference electrode as the negative active material. Other materials having cycling potentials that exceed that of lithium by several hundred millivolts and which may be suitable for use as the negative active material include the materials listed in Table 1. Such materials may be used alone or in combination with the lithium titanates described above and/or any of the other materials listed in Table 1.

TABLE 1

| | | Cycling Potentials (vs Li) | | |
|---|---|---|---|---|
| Class | Compound | Vmin | Vmax | Vavg |
| Oxides | TiO$_2$ (B) | 0.8 | 2.0 | 1.45 |
| Oxides | TiO$_2$ (Anatase) | 1.4 | 2 | 1.80 |
| Oxides | WO$_2$ | 0.6 | 1.3 | 0.80 |
| Oxides | WO$_3$ | 0.5 | 2.6 | 1.0 |
| Oxides | MoO$_2$ | 1.3 | 2 | 1.60 |

TABLE 1-continued

| | | Cycling Potentials (vs Li) | | |
|---|---|---|---|---|
| Class | Compound | Vmin | Vmax | Vavg |
| Oxides | Nb$_2$O$_5$ | 1.0 | 2 | 1.50 |
| Oxides | LiWO$_2$ | | | 0.75 |
| Oxides | Li$_x$MoO$_2$ | 0.8 | 2 | 1.60 |
| Oxides | V$_6$O$_{13}$ | | | 2.30 |
| Oxides | Li$_6$Fe$_2$O$_3$ | | | 0.75 |
| Oxides | LiFeO$_2$ | 1.0 | 3.0 | 2.0 |
| Oxides | Fe$_2$O$_3$ | 0.2 | 2.0 | 0.75 |
| Oxides | MO where M = Co, Ni, Cu or Fe | | | 0.8-1.5 |
| Sulfides | FeS$_2$ | 1.3 | 1.9 | 1.65 |
| Sulfides | MoS$_2$ | | | 1.75 |
| Sulfides | TiS$_2$ | | | 2.00 |
| Alloys | Sn—Bi | | | 0.75 |
| Alloys | Alloys comprising of Al, Si or Sn and other elements | | | 0.30 |
| Alloys | Sn—Co—C | | | 0.30 |
| Alloys | Sb | | | 0.90 |
| Alloys | NbSe$_3$ | | | 1.95 |
| Alloys | Bi | | | 0.80 |
| Alloys | In | | | 0.60 |
| Alloys | LixAl | | | 0.36 |
| Alloys | LixSn | 0 | 1.3 | 0.50 |
| Alloys | Sn—Sb | | | 0.0-1.0 |
| Polymers | Poly(phenylquinoline) | | | 1.50 |
| Polymers | Polyparaphenylene | | | 0.70 |
| Polymers | Polyacetylene | | | 1.00 |
| Vanadates | Li$_x$MVO$_4$ where M = Ni, Co, Cd, Zn | | | 2.0-0.5 |

A binder material may also be utilized in conjunction with the layer of active material 224. For example, according to an exemplary embodiment, the layer of active material may include a binder such as polyvinylidine fluoride (PVDF) or an elastomeric polymer. The active material 224 may also include a conductive material such as carbon (e.g., carbon black) at weight loadings of between zero and ten percent to provide increased electronic conductivity.

According to various exemplary embodiments, the thickness of the active material 224 is between approximately 0.1 μm and 3 mm. According to other exemplary embodiments, the thickness of the active material 224 may be between approximately 25 μm and 300 μm. According to another exemplary embodiment, the thickness of the active material 224 may be between approximately 20 μm and 90 μm, and according to a particular exemplary embodiment, approximately 75 μm.

Lithium plating occurs when the potential of the negative electrode versus a lithium reference electrode reaches 0 volts, and is a well-known phenomenon that can lead to loss in performance of lithium-ion batteries. When used in a negative electrode of a lithium-ion battery, lithium titanate active materials cycle lithium at a potential plateau of about 1.55 volts (which is substantially higher than graphitic carbon, which cycles lithium at approximately 0.1 volts in the fully charged state). As a result, batteries using lithium titanate as a negative active material are less susceptible to lithium plating than those using carbon-based materials for the negative active material.

One advantageous feature of utilizing a negative electrode active material such as a lithium titanate material or another material having an average potential that is greater or equal to approximately 0.2 V versus Li/Li+ is that more favorable design rules may be possible for rechargeable (i.e., secondary) lithium-ion batteries. One such design rule relates to cell balance parameters.

Cell balance refers to the ratio of the negative electrode capacity to the positive electrode capacity. Thus, the cell balance γ (gamma) can be expressed as an equation having the form:

$$\gamma = \frac{Q_{neg}}{Q_{pos}}$$

where $Q_{neg}$ is the capacity of the negative electrode and is equal to the product of the amount of negative electrode material, the percentage of the active material contributing to the capacity, and the specific capacity of the active material and $Q_{pos}$ the capacity of the positive electrode and is equal to the product of the amount of positive material, the percent of the active material contributing to the capacity, and the specific capacity of active material. According to an exemplary embodiment in which a lithium titanate negative active material and a lithium cobalt oxide positive active material are used, the specific capacity of the negative active material may be 165 mAh/g (at C/3-C/1, between 1.2 and 2.0 volts versus Li) and the specific capacity of the positive active material may be 150 mAh/g (at C/3-C/1, between 4.25 and 3.0 volts versus Li).

Cell balance dictates the mass (deposition) ratio of the two electrodes. In conjunction with charge cutoff voltage, cell balance determines what fraction of the active Li sites in the two electrode materials is utilized during charge and discharge. For example, in a negative-limited design, nearly all active Li sites in the negative material are utilized in the negative electrode, but only a fraction of the active sites in the positive electrode are utilized. The chosen cell balance hence determines the specific capacity delivered by both electrodes, and the stability of their performance for repeated cycling. Primary considerations for choosing the cell balance include safety, delivered capacity, and capacity fade under regular cycling and deep discharge conditions.

Rechargeable lithium-ion batteries using carbon-based negative active materials are typically fabricated such that the capacity of the electrodes is balanced (i.e., the capacities of the positive electrode and negative electrode are equal) or positive-limited (i.e., the capacity of the positive electrode is less than that of the negative electrode). The reason for this design rule is that if the battery was negative-limited, the voltage of the negative electrode versus a lithium reference electrode would drop to near zero volts during charging of the battery, which may result in lithium plating (since carbonaceous negative electrodes typically operate very close to the potential of metallic lithium (0.1-0.2 volts versus a lithium reference electrode), a further decrease in potential at the negative electrode would result in plating of lithium).

According to an exemplary embodiment in which a battery utilizes a negative electrode active material such as a lithium titanate material or another material having an average potential that is greater or equal to approximately 0.2 volts versus a lithium reference electrode, rechargeable lithium-ion batteries may be fabricated with a negative-limited design in which the capacity of the negative electrode is less than that of the positive electrode. For example, for a lithium titanate active material having a potential plateau of approximately 1.55 volts, a cell balance of between approximately 0.80 to 0.93 may be used (i.e., the nominal capacity of the negative electrode may be between 80 and 93 percent of the nominal capacity of the positive electrode; stated another way, the ratio of the positive electrode capacity to the negative electrode capacity is between approximately 1.07 and 1.25). According to another exemplary embodiment, the cell balance may be less than approximately 0.8 (e.g., 0.73) (that is, the ratio of the positive electrode capacity to the negative electrode capacity may be greater than 1.25). According to another exemplary embodiment, the cell balance may be approximately 0.85 (ratio of the positive electrode capacity to the negative electrode capacity of approximately 1.176). According to another exemplary embodiment, the cell balance may be approximately 0.84 (ratio of the positive electrode capacity to the negative electrode capacity of approximately 1.19). According to another exemplary embodiment, the cell balance may be approximately 0.93 (ratio of the positive electrode capacity to the negative electrode capacity of approximately 1.075). According to another exemplary embodiment, the cell balance may be less than approximately 0.90 (ratio of the positive electrode capacity to the negative electrode capacity of approximately 1.11).

The inventors have unexpectedly discovered that negative-limited rechargeable lithium-ion batteries (where the negative electrode active material is a lithium titanate material or another material having an average potential that is greater or equal to approximately 0.2 volts versus a lithium reference electrode) exhibit lower capacity fade and lower power fade due to reduced likelihood of over-charging of the positive electrode.

Figure 3:
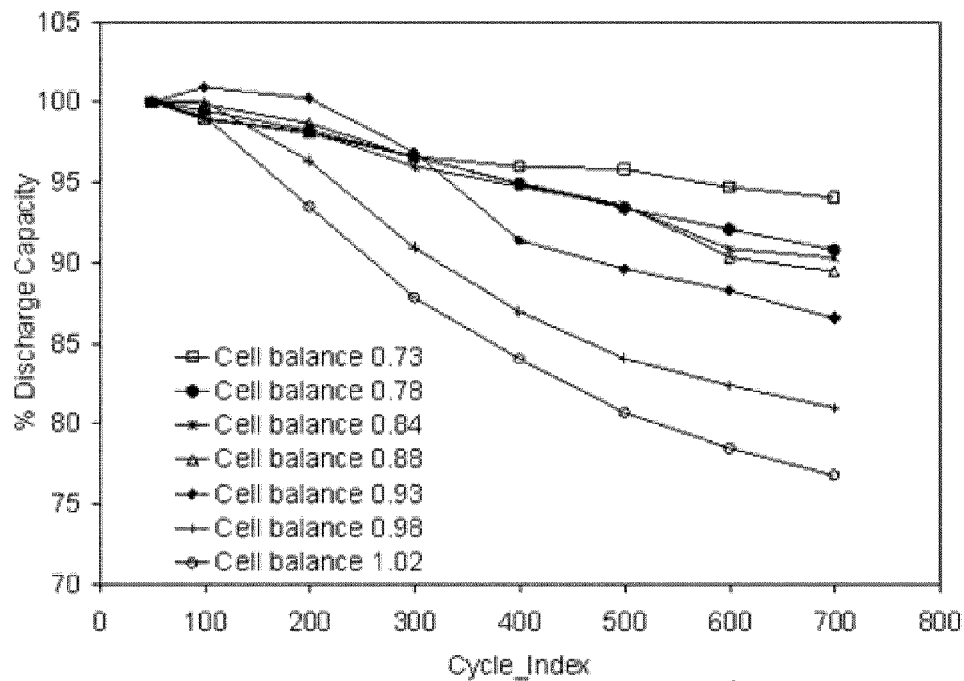
FIG. 3 is a graph illustrating the capacity fade as a function of cell balance for batteries having a variety of cell balances.

FIG. 3 is a graph illustrating the capacity fade behavior for batteries having cell balances of 0.73, 0.78, 0.84, 0.88, 0.93, 0.98, and 1.02 (all batteries utilized $LiCoO_2$ as a positive active material and $Li_4Ti_5O_{12}$ as a negative active material). The batteries were subjected to 700 charge and discharge cycles over the course of an eight month period, and the discharge capacity of each of the batteries was measured after each cycle. For clarity, FIG. 3 illustrates the discharge capacities of each of the cells only for every $100^{th}$ cycle, and is expressed as a percentage of the original discharge capacities for the cells (e.g., a new battery would have 100% of its capacity, and as the battery is cycled, its capacity is some lower percentage of the original discharge capacity).

Figure 4:
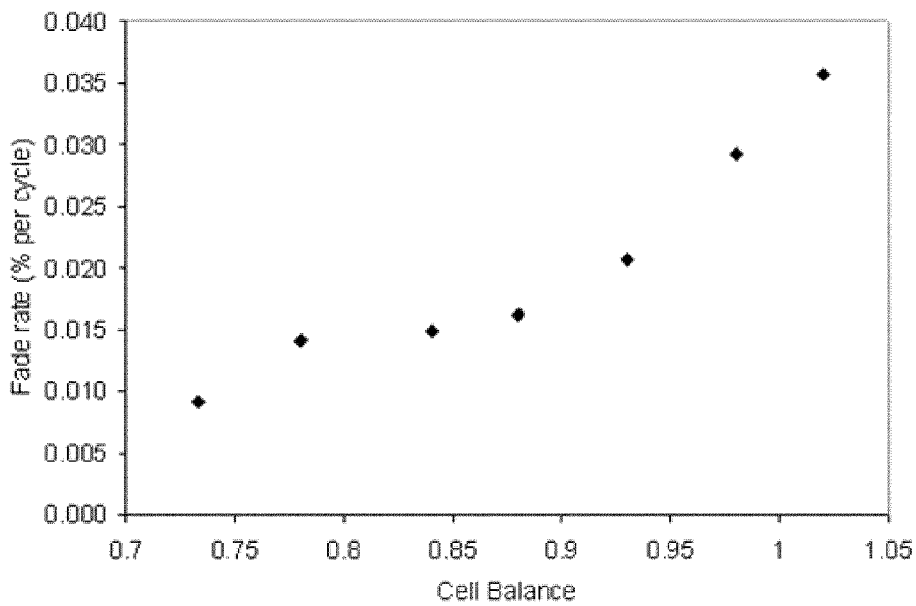
FIG. 4 is a graph illustrating the fade rate as a function of cell balance for the batteries described with respect to FIG. 3.

As illustrated in FIGS. 3 and 4, batteries that had lower cell balances retained a greater amount of their original discharge capacity with repeated charge and discharge cycling. Stated another way, the greater the cell imbalance (i.e., the more negative-limited the batteries were), the better the batteries resisted capacity fade with increased cycling. For example, as shown in FIG. 4, the percentage of capacity fade per cycle was significantly less for the battery having a 0.73 cell balance as compared to the battery having a 0.98 cell balance. It should be noted that although FIG. 3 appears to show a capacity increase above 100% for the 0.93 cell balance batteries, this is a result of an experimental artifact and should not be interpreted to mean that the discharge capacity of this battery increased above 100% of its original discharge capacity.

Figure 5:
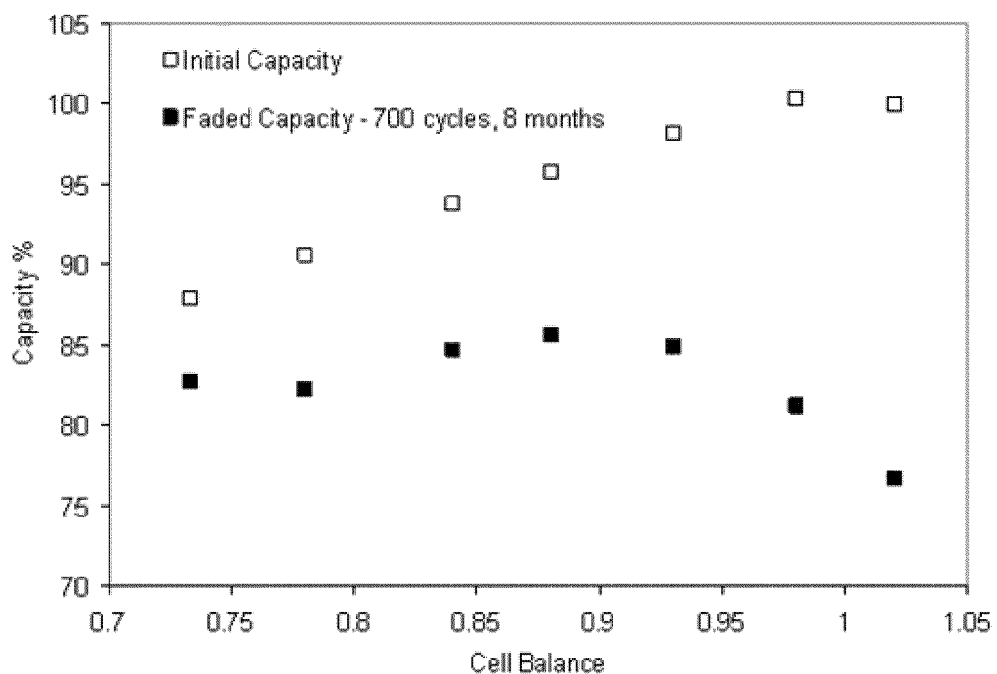
FIG. 5 is a graph illustrating the initial capacities the batteries described with respect to FIGURE and the capacities of such batteries after 700 charge and discharge cycles over a period of eight months.

One consequence of fabricating negative-limited batteries of the type described above is that such batteries initially have lower overall discharge capacities than balanced batteries (i.e., batteries having a cell balance of 1.0). For example, FIG. 5 is a graph illustrating the relationship between cell balance and the initial overall battery capacities and the "faded" capacities (i.e., the capacities after the batteries were subjected to 700 charge and discharge cycles over the course of eight months) for batteries having cell balances of 0.73, 0.78, 0.84, 0.88, 0.93, 0.98, and 1.02. The capacities are shown as percentages of the capacity that a balanced cell would be expected to exhibit. As shown in FIG. 5, increasing the cell imbalance (i.e., making batteries more negative-limited) results in lower initial capacity.

The inventors have unexpectedly found, however, that although negative-limited batteries may have lower initial capacities than balanced cells, the more negative-limited batteries may actually have higher capacities than balanced batteries after repeated cycling due to their improved resistance to capacity fade. As shown in FIG. 5, after 700 charge/discharge cycles over the course of eight months, the batteries having cell balances of 0.98 and 1.02 actually have lower discharge capacities than the batteries having cell balances of 0.73, 0.78, 0.84, 0.88 and 0.93. As a result, rechargeable lithium-ion batteries may be fabricated with a negative-limited cell imbalance that requires less negative active material without sacrificing long-term performance of the batteries.

Figure 6:
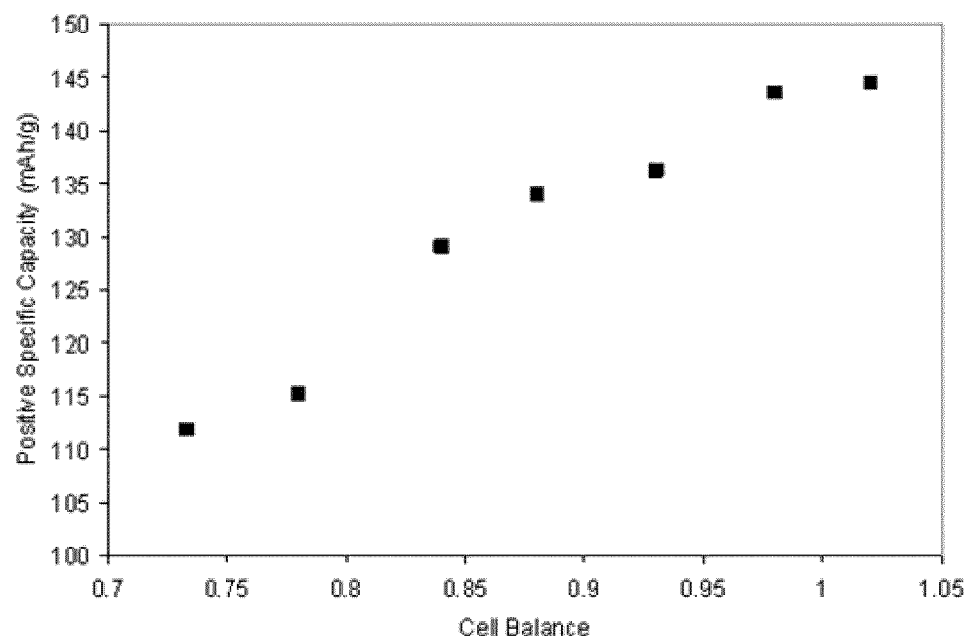
FIG. 6 is a graph illustrating the specific capacity of the positive electrode as a function of cell balance for the batteries described with respect to FIG. 3.

FIG. 6 illustrates the specific capacity of the positive electrode as a function of cell balance for the batteries having cell balances of 0.73, 0.78, 0.84, 0.88, 0.93, 0.98, and 1.02. This shows that with lower cell balance, a lower specific capacity of the positive is obtained. In other words, with a lower cell balance, the positive electrode is less stressed (worked), which leads to lower capacity fade. It should be noted that the data shown in FIG. 6 correlates well with the data shown in FIG. 4, which emphasizes the link between positive specific capacity and capacity fade.

As a battery ages, both the negative electrode and the positive electrode fade in capacity. The rate at which the negative and positive electrodes fade individually will affect the overall cell balance. For example, if the positive electrode fades at a greater rate than the negative electrode, the battery will shift toward being less negative-limited (i.e., the cell balance will increase with aging), and if the negative electrode fades at a greater rate than the positive electrode, the battery will shift toward being more negative-limited (i.e., the cell balance will decrease with aging). It is thus possible that a battery that starts off as being negative-limited may eventually become positive-limited if the positive electrode fades at a greater rate than the negative electrode (and a positive-limited battery may become negative-limited if the negative electrode fade rate exceeds that of the positive electrode fade rate).

It should be noted, however, that the capacity of the battery, and thus the overall fade rate for the battery, will be determined by the limiting electrode. That is, the overall fade rate for a negative-limited battery will be determined by the fade rate of the negative electrode. Not until the battery goes from being negative-limited to positive-limited will the fade rate of the battery be driven by the positive electrode fade rate.

By way of example, a battery having a positive electrode capacity of 100 mAh and a negative electrode capacity of 90 mAh will have an overall cell capacity of 90 mAh. After a period of time, the positive electrode capacity may decrease to 95 mAh while the negative electrode capacity may decrease to 89 mAh, in which case the overall cell capacity will be 89 mAh. Here the positive electrode would have faded five times more than the negative electrode, but because the battery fade is limited by the negative electrode, the overall battery fade was one-fifth what it would have been if the positive electrode determined the capacity of the battery. In contrast, if this battery continues to age to a point where it is positive-limited, then the capacity fade of the battery will be driven by the positive electrode. For example, if the battery ages to the point where the negative electrode capacity is 87 mAh (a decrease of 3 mAh from the original 90 mAh) and the positive electrode capacity drops to 80 mAh (a decrease of 20 mAh), the battery will be positive-limited. If at a later time the negative electrode capacity drops to 86 mAh and the positive electrode capacity drops to 75 mAh, the capacity of the battery will be 75 mAh. That is, the quicker-fading electrode now determines the capacity of the battery such that the slower-fading electrode will not constrain the overall capacity fade for the battery.

To reduce the overall capacity fade rate for a battery, then, it is desirable to limit the battery by the slowest-fading electrode and to prevent the cell balance from switching during the useful life of the battery (or to at least significantly delay the switch from occurring). One further consideration to take into account is the fact that it is expected that the fade rate of the quicker-fading electrodes will actually accelerate as the cell approaches a balanced condition. This suggests that there is a compound benefit to increasing the cell imbalance to limit the cell to the slower-fading electrode (e.g., making a cell more negative-limited where the negative electrode fades more slowly than the positive electrode), since there will be a non-linear relationship between the initial cell balance and the time (or number of charge-discharge cycles) it takes for the battery to switch over to being limited by the quicker-accelerating electrode.

According to various exemplary embodiments described herein that use negative electrode active materials that cycle lithium at a voltage greater than approximately 0.2 V versus a lithium reference electrode (for example, a lithium titanate material such as $Li_4Ti_5O_{12}$), the fade rate of the positive electrode is greater than that of the negative electrode. Accordingly, it is advantageous to provide a battery that is negative-limited, and the more negative-limited the battery is, the better it is expected will be the resistance to overall battery capacity fade. Indeed, this is consistent with the results shown in FIG. 2. Reducing the fade rate for these batteries is particularly beneficial for applications with very long product life cycles and where good forecast of capacity fade is essential (such as implanted medical device).

Another advantageous feature of negative-limited batteries such as those described herein is that such batteries do not require electrolyte additives that are intended to prevent degradation due to oxidation of the positive electrode. For example, in balanced batteries or batteries having excess positive electrode capacity, additives such as biphenyl are included in the electrolyte. Besides the obvious disadvantage that the inclusion of such additives increases the cost of the batteries, the additives also complicate the electrolyte chemistry and typically lead to gas formation and swelling when oxidized. Eliminating the additives may thus reduce the cost of producing the battery, simplify the electrolyte chemistry, and reduce the amount of gas formation and battery swelling that may occur with repeated cycling of the battery.

Yet another advantageous feature of the use of negative-limited designs is that higher energy densities may be achieved as compared to balanced cells. Negative active materials such as lithium titanate have lower energy densities than positive active materials such as $LiCoO_2$ (i.e., for equal volumes of $Li_4Ti_5O_{12}$ and $LiCoO_2$, the $LiCoO_2$ will have more active lithium that contributes to the battery capacity). As a result, altering the cell balance to a negative-limited design may have a substantial effect on the volume required for the negative active material for a given amount of positive active material. This may allow for the production of smaller batteries for the same amount of positive active material. These smaller batteries may also exhibit improved energy density as compared to larger balanced cells. For example, as described with respect to FIG. 4, negative-limited cells would be expected to have higher capacities than balanced cells after repeated cycling (e.g., for 500 charge/discharge cycles); smaller negative-limited batteries having higher capacities would have a higher energy density than the larger balanced cells.

Negative-limited cells may also provide cost savings as compared to balanced cells. As previously described, certain electrolyte additives may be omitted from the negative-limited cells. Other materials savings may be realized as a result of using less negative active material and/or producing smaller batteries (e.g., the container may be smaller, which would require less material).

One particular advantage associated with negative-limited batteries (using negative active materials such as a lithium titanate material or another material having an average potential that is greater or equal to approximately 0.2 volts versus a lithium reference electrode) is described with respect to FIGS. 5-9. According to an exemplary embodiment, an improved formation process may be used in conjunction with such batteries that provides enhanced tolerance to repeated deep discharge conditions, as evidenced, for example, by improved resistance to capacity fade.

Figure 7:
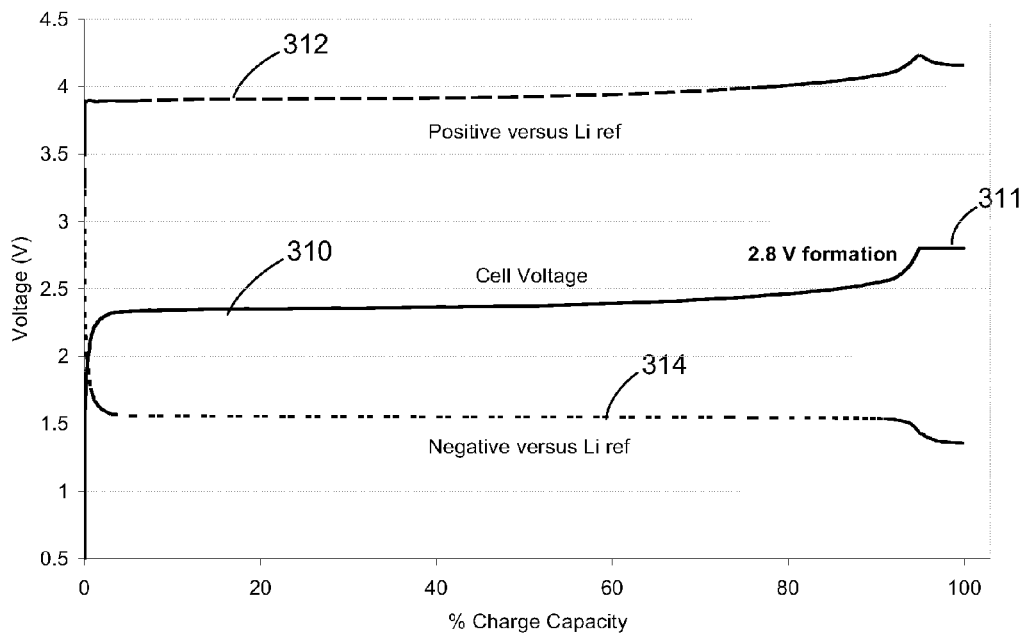
FIG. 7 is a graph illustrating the battery voltage and the voltage of the positive and negative electrodes versus a lithium reference electrode during a battery formation process in which a charging voltage of 2.8 volts is used.

During a formation (i.e., initial charging of the battery) process, lithium-ion batteries are charged at a relatively low rate (such as C/10 or slower) to the maximum operating voltage of the battery. By way of example, for a lithium-ion battery ($LiCoO_2$ positive active material, lithium titanate negative active material) that is configured to have an intended operating voltage range between approximately 2.8 volts (full charge) and 1.8 volts (discharge cut-off voltage), a formation process might involve charging the battery at a voltage of 2.8 volts at a rate of C/10 and then holding the battery at the 2.8 volt level for four hours. FIG. 7 illustrates the voltage behavior for a battery undergoing such a formation process, and includes a curve 310 representative of the overall battery voltage, a curve 312 representative of the positive electrode potential versus a lithium reference electrode, and a curve 314 representative of the negative electrode potential versus a lithium reference electrode. As shown in FIG. 7, the overall battery voltage gradually increases to a 2.8 volt plateau 311 at the end of formation process, while the negative electrode potential versus a lithium reference electrode drops to a level of between approximately 1.3 and 1.4 volts toward the end of curve 314.

The formation process described in the preceding paragraph may result in a relatively low irreversible capacity loss for the battery (e.g., between approximately 6 and 11 percent) during the formation process. This irreversible capacity loss results primarily from the passivation of either of the two electrodes, and occurs when otherwise cyclable lithium ions in the battery (i.e., lithium ions that shuttle between the positive and negative electrodes during charging and discharging) fail to combine in a reversible way with an electrode active material.

Figure 8:
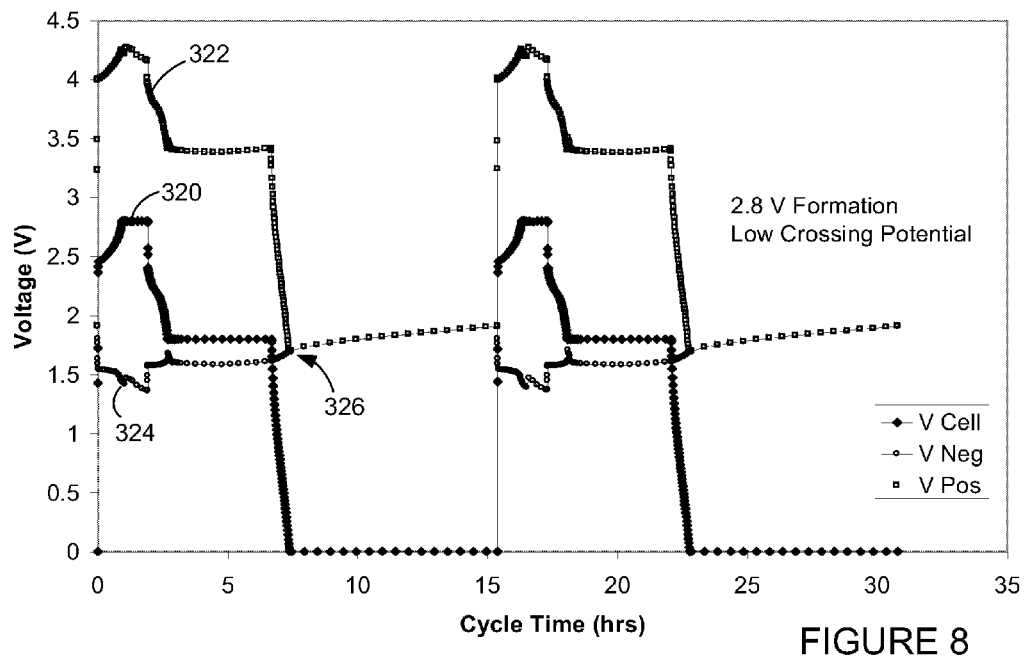
FIG. 8 is a graph illustrating two deep discharge cycles for a battery manufactured using the formation process according to FIG. 5.

FIG. 8 illustrates the voltage behavior for the battery when it is subjected to two deep discharge cycles where the battery is discharged to zero volts, and includes a curve 320 representative of the overall battery voltage, a curve 322 representative of the positive electrode potential versus a lithium reference electrode, and a curve 324 representative of the negative electrode potential versus a lithium reference electrode. As the overall battery voltage drops toward zero volts (i.e., a deep discharge condition), the curves 322, 324 representing the potentials of the positive and negative electrodes converge toward and intersect at a point 326 referred to as the zero volt crossing potential for the battery. As illustrated in FIG. 8, the zero voltage crossing potential for this battery occurs at a point where the positive electrode potential versus a lithium reference electrode is less than 2.0 volts (e.g., between approximately 1.6 and 1.8 volts).

Figure 11:
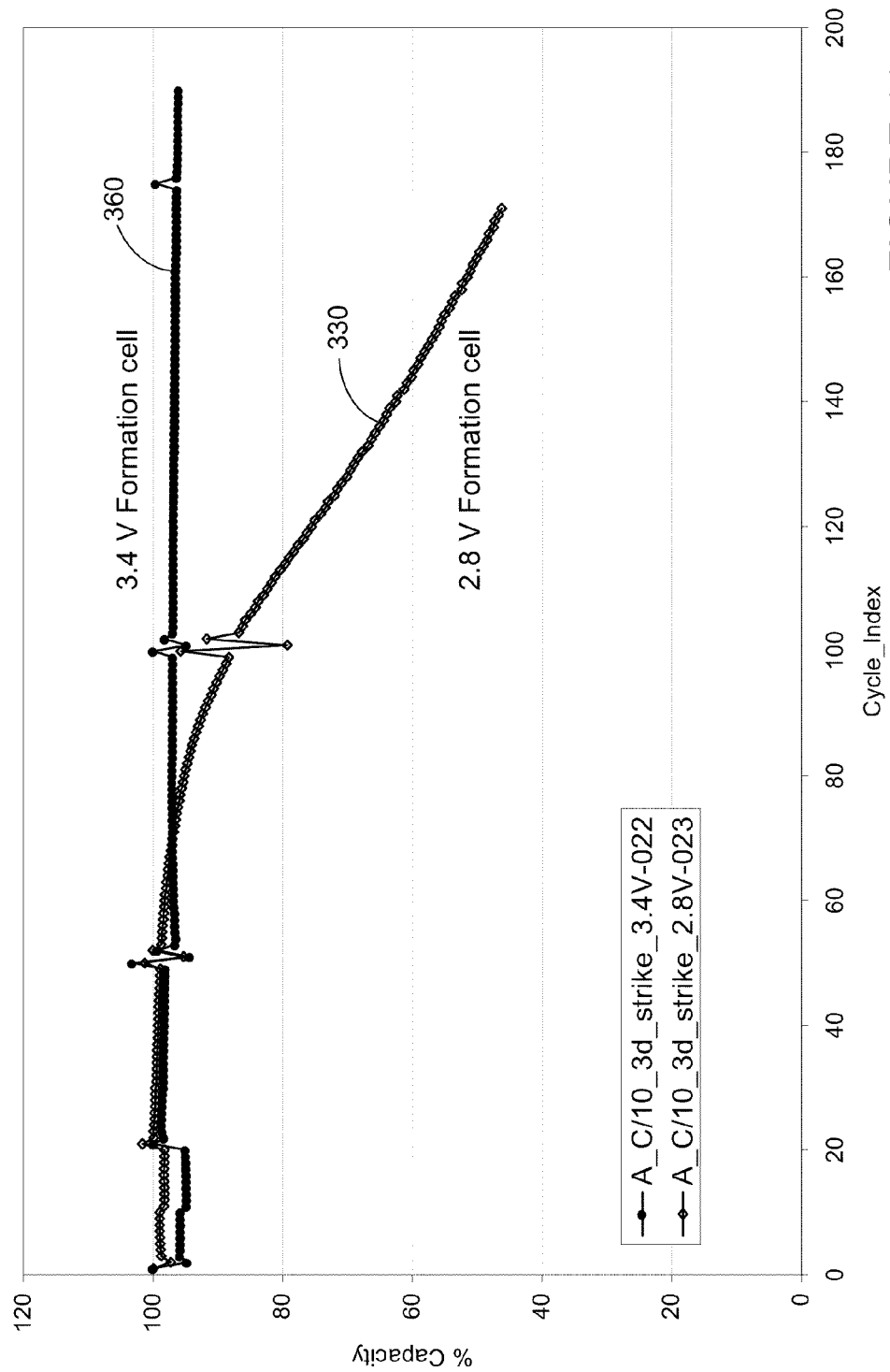
FIG. 11 is a graph illustrating the resistance to capacity fade for the batteries produced using the formation processes according to FIGS. 5 and 7.

FIG. 11 is a graph that includes a curve 330 representative of the discharge capacity of the battery as it undergoes repeated deep discharge cycles. The variations in the curves at cycles 50 and 100 are a result of two characterization cycles that were run during the test. These characterization cycles consist of (1) a slow rate cycle to determine trends in full charge/discharge capacity, (2) an application rate cycle to determine impact of repeated deep discharge on performance in normal application conditions. Other smaller variations (such as around cycle 170) are experimental artifacts.

As illustrated by the curve 330 shown in FIG. 11, the discharge capacity of the battery drops as it is subjected to repeated deep discharge cycles. This capacity fade with repeated deep discharge cycles results in a battery that must be recharged more frequently, since the battery does not hold as much charge as it did after initial formation.

The inventors have determined through experimentation that one factor that contributes to the capacity fade is that the positive active material (in this case $LiCoO_2$) tends to relatively rapidly degrade when driven to a potential versus a lithium reference electrode that is less than 2.0 volts (e.g., approximately 1.6 volts). It should be noted that where different positive active materials are used, degradation of such materials may occur at a different level. As illustrated in FIG. 8, the potential of the positive electrode versus a lithium reference electrode, as represented by curve 322, drops to a level that is below 2.0 volts as the battery is discharged to a near-zero-volt charge state and the curves 322, 324 approach the zero volt crossing potential 326 for the battery.

The inventors have surprisingly discovered that the resistance to capacity fade for a negative-limited battery that utilizes a lithium titanate active material on the negative electrode can be significantly improved by using a formation process in which the charging voltage is greater than the normal fully charged voltage of the battery, with no associated increase in charging rate (e.g., the same C/10 charging rate may be used as described in the preceding example).

Figure 9:
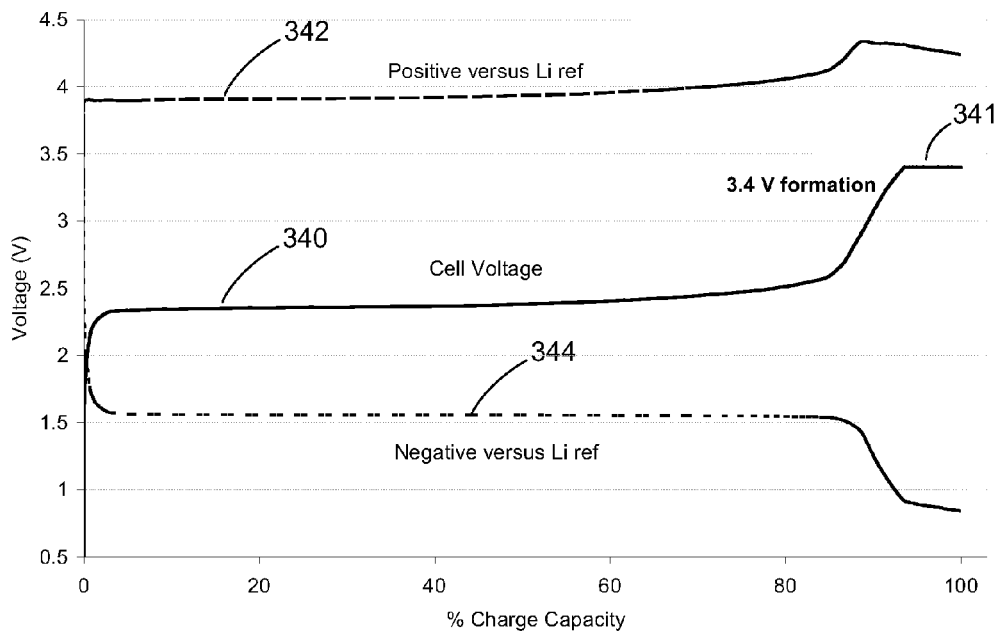
FIG. 9 is a graph illustrating the battery voltage and the voltage of the positive and negative electrodes versus a lithium reference electrode during a battery formation process in which a charging voltage of 3.4 volts is used.

According to an exemplary embodiment, a lithium-ion battery ($LiCoO_2$ positive active material, lithium titanate negative active material) having an intended operating voltage range from 2.8 volts (fully charged state) to 1.8 volts (discharge cut-off voltage) is subjected to a formation process that utilizes a charging voltage of between approximately 3.4 volts and 3.8 volts at a C/10 charge rate, after which the battery voltage is held at this level for a period of between approximately 4 and 12 hours. FIG. 9 illustrates the voltage behavior for a battery undergoing such a formation process, and includes a curve 340 representative of the overall battery voltage, a curve 342 representative of the positive electrode potential versus a lithium reference electrode, and a curve 344 representative of the negative electrode potential versus a lithium reference electrode.

As shown in FIG. 9, the battery voltage gradually increases to a 3.4 volt plateau 341 at the end of formation process. The higher charging voltage during the formation process results in a greater amount of irreversible capacity loss as compared to formation process using a lower charging voltage (e.g., 2.8 volts). For example, the total irreversible capacity loss obtained using the higher-voltage formation process is expected to be between approximately 12 and 20 percent, depending on factors including, for example, the selected cut-off voltage and hold duration.

The negative electrode potential versus a lithium reference electrode drops to a level below approximately 0.9 volts (e.g., between approximately 0.5 and 0.8 volts) as the battery reaches its fully charged state (i.e., the charge top-off voltage during normal use), while the positive electrode potential does not exhibit a large voltage increase. This is primarily due to the fact that the battery is negative-limited such that the capacity of the negative electrode is less than that of the positive electrode (i.e., the negative electrode depletes before the positive electrode, which results in a potential drop for the negative electrode).

As the potential of the negative electrode drops below approximately 0.9 volts, a reaction takes place in which the solvent component of the electrolyte (e.g., ethylene carbonate) reduces. In this reduction reaction, a passive film (e.g., lithium carbonate or lithium alkyl carbonate) is formed on the negative electrode. Additionally, an additive such as carbon or a carbon-based material may be provided in the negative active material to assist in the formation of the passive film and to increase the amount of lithium that reacts irreversibly to form the film (e.g., between approximately 5 and 10 volume percent carbon may be provided in the lithium titanate material).

One advantageous feature of the reduction reaction is that the increased irreversible capacity loss of the battery tends to increase the zero volt crossing potential for the battery, which allows for enhanced resistance to capacity fade since the higher zero volt crossing potential is above the level where the positive active material degrades.

Figure 10:
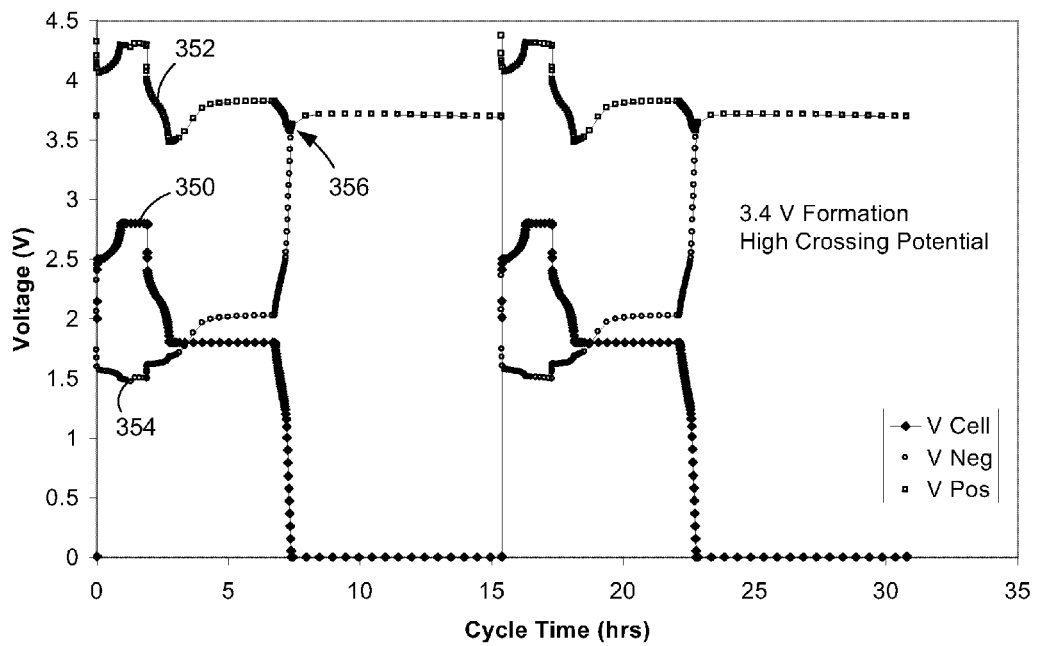
FIG. 10 is a graph illustrating two deep discharge cycles for a battery manufactured using the formation process according to FIG. 7.

FIG. 10 illustrates the voltage behavior for such a battery when it is subjected to two deep discharge cycles where the battery is discharged to zero volts, and includes a curve 350 representative of the overall battery voltage, a curve 352 representative of the positive electrode potential versus a lithium reference electrode, and a curve 354 representative of the negative electrode potential versus a lithium reference electrode. As the overall battery voltage drops toward zero volts (i.e., a deep discharge condition), the curves 352, 354 representing the potentials of the positive and negative electrodes converge toward and intersect at the zero volt crossing potential 356 for the battery. As illustrated in FIG. 10, the zero voltage crossing potential for this battery occurs at a point where the positive electrode potential versus a lithium reference electrode is greater than approximately 3.5 volts, which is above the threshold at which the positive active material ($LiCoO_2$) would be expected to degrade. It should also be noted that the lithium titanate negative electrode active material is also stable at this potential.

The battery produced using the high-voltage formation process exhibits significantly enhanced resistance to capacity fade when subjected to repeated deep discharge cycles, as illustrated by the curve 360 in FIG. 11. The capacity of the battery is substantially constant over approximately 170 deep discharge cycles, in contrast to the relatively significant capacity fade exhibited by the battery using a more conventional formation process (curve 330).

Accordingly, the use of a voltage that exceeds the voltage of the fully charged battery during the formation process acts to induce a larger amount of irreversible capacity loss in the battery than would otherwise be obtained. This in turn increases the zero voltage crossing potential for the battery above the level where the positive active material would degrade. As a result, the resistance to capacity fade with repeated deep discharge cycles is enhanced.

Example 1

Lithium ion cells having nominal capacities of approximately 0.15 ampere hours (Ah) were prepared having a lithium cobalt oxide ($LiCoO_2$) active material on the positive electrode and a lithium titanate active material on the negative electrode. The electrolyte used included a mixture of ethylene carbonate, ethylmethyl carbonate, and 1 molar $LiPF_6$ as the lithium salt. The cells were constructed as spirally wound prismatic cells hermetically sealed in a stainless steel can with a glass feedthrough.

The negative and positive electrodes for the cells were prepared via a slurry coating and calendaring process. Both electrodes included the aforementioned active material, a conductive carbon additive, and organic binder. The mass loading (grams of materials per unit area) during the slurry coating process was controlled on both electrodes to attain a mass ratio of the two active materials to be 0.71. Based on the nominal specific capacities of the two active materials, determined via half cell testing (150 mAh/g for lithium cobalt oxide, 165 mAh/g for lithium titanate), the cell balance of this cell was 0.78 (i.e., the nominal capacity of the negative electrode was 78% of the nominal capacity of the positive electrode).

Cells built with the above design were subjected to a conventional formation process in which the cells were charged at C/10 (15 mA) to the normal cut-off voltage of 2.8 volts and were held potentiostatically at 2.8 volts for 4 hours. Another group of cells built with the above design were subjected to an improved high voltage formation process. In this process, the cells were charged at C/10 (15 mA) to 3.4 volts and were held potentiostatically at 3.4 volts for 4 hours. After these respective formation processes, both groups of cells were discharged at C/10 to 1.8 volts and held at 1.8 volts for 4 hours.

The capacities delivered by the cells were measured both during the formation charge process and during the discharge process. The measured capacity values are given in Table 2. The formation charge capacity is typically greater than the discharge capacity, which is indicative of the irreversible capacity loss accounted for by the irreversible processes. The cells show 6.5% irreversible capacity during the conventional formation process, compared to 12.2% in the improved high voltage formation process. Thus, the difference in the irreversible capacities is approximately 5.7% between the 2.8 volts formation and high voltage 3.4 volts formation. This difference is seen to increase as a greater voltage and/or a longer potentiostatic hold duration is chosen. It is noteworthy that this greater irreversible capacity does not reduce the reversible capacity of the cell. Cycle 1 discharge capacity is the same for both groups of cells, as shown in Table 2. The higher irreversible capacity is attained by extending the voltage window beyond its normal cut-off and thus comes out from the extended capacity and not from the nominal capacity over the voltage range for normal cycling. Thus, unlike typical cases where higher irreversible capacity means lower reversible capacity, such a lowering of the reversible capacity was not observed.

TABLE 2

|  | Cycle 1 charge capacity (Ah) | Cycle 1 discharge Capacity (Ah) | Cycle 160 charge capacity (Ah) | Cycle 160 discharge capacity (Ah) | % Fade between cycles 1 and 160 |
|---|---|---|---|---|---|
| Cells formed at 2.8 volts | 0.168 | 0.157 | 0.081 | 0.081 | 48.4% |
| Cells formed at 3.4 volts | 0.180 | 0.158 | 0.152 | 0.152 | 3.5% |

These cells were then cycled between 2.8 volts to 0.0 volts to determine the stability of performance for repeated deep discharge to zero volts. During the charge phase of this cycling, the cells were taken to 2.8 volts at a 1C rate (150 mA) and potentiostatically held at 2.8 volts for 1 hour. During the discharge phase of the cycling, the cells were taken to 0.0 volts in a staged manner—first the cells were discharged to 1.8 volts at 150 mA, held potentiostatically at 1.8 volts for 1 hour, then discharged to 0.0 volts at 0.1 mA and finally held potentiostatically at 0.0 volts for 24 hours. The difference in performance of the two groups of cells in this test is shown in FIG. 9, where the capacity obtained in every cycle as a percent of the initial capacity is plotted versus the cycle number. The cells with the conventional formation show large capacity fade, with the capacity falling to approximately 52% after 160 deep discharge cycles. In sharp contrast, the cells with the high voltage formation continue to show greater than 95% of the initial capacity after 160 deep discharge cycles.

Rechargeable lithium-ion cells that utilize lithium titanate as a negative electrode active material may provide enhanced tolerance to overdischarge conditions (e.g., conditions in which the lithium-ion batteries are repeatedly cycled to near-zero volt conditions), as described in U.S. patent application Ser. No. 10/979,040 filed Oct. 29, 2004 (the entire disclosure of which is incorporated by reference herein) and Example 2 below.

Example 2

This example illustrates the overdischarge performance of lithium ion batteries utilizing a negative electrode having $Li_4Ti_5O_{12}$ active material coated onto an aluminum current collector as compared to the performance of lithium ion batteries in which a carbon active material (graphitized MCMB) is coated onto a copper current collector. In all cases, the electrodes were cycled against positive electrodes having a $LiCoO_2$ active material with a capacity of 5.53 mAh coated on an aluminum current collector.

Negative electrodes were produced by mixing lithium titanate (commercially available from Süd Chemie Corporation) with a poly(vinylidine fluoride) binder, carbon black and 1-methyl-2-pyrolidone (NMP) into a slurry and depositing the mixture onto an aluminum foil current collector and drying on a heated drum. The active weight percent of the dried coating was 89.25%. Three coating deposition levels of the coating were used: 17.37, 18.78 and 20.69 mg/cm². Based on the theoretical specific capacity of $Li_4Ti_5O_{12}$ (155 mAh/g), the capacity of these electrodes was 4.76, 5.14 and 5.67 mAh, respectively. Thus, when cycled against the positive electrodes, the cell balance (i.e., the ratio of the negative and positive electrode capacities) was 0.85, 0.93 and 1.02, respectively.

After drying, the electrode coatings were calendared to a density of about 2.2 g/cm³ and cut into circular disks having an area of 1.98 cm². Lithium ion cells were produced by assembling these electrodes into type-2032 coin cell hardware. A microporous polyolefin separator was used to separate the negative and positive electrodes, and the cells were activated by the addition of electrolyte consisting of 1 M $LiPF_6$ in a mixture of propylene carbonate, ethylene carbonate and diethyl carbonate.

Comparative cells were manufactured in identical fashion, with the exception of the fact that the negative electrodes utilized graphite active material (mesocarbon microbeads) coated on copper foil.

Cells were charged and discharged at a rate of 0.2 mA using an ARBIN BT2000 battery cycler. For the first four cycles, the cells were cycled over a normal operating voltage range (3.0 to 1.8 V for the $Li_4Ti_5O_{12}$ cells, 4.075 to 2.75 volts for the comparative cells). After completing four cycles, the cells then underwent four overdischarge cycles, where they were discharged to 0 volts and charged back to their normal charge voltage. The overdischarge took place as a sequence of steps at progressively lower currents: 0.2 mA down to 1.8 volts, 0.05 mA to 1.0 volts and 0.01 mA to 0 volts. Following the overdischarge cycles, the cells were then cycled over the original voltage range to measure the recovered capacity for the cells.

Figure 12:
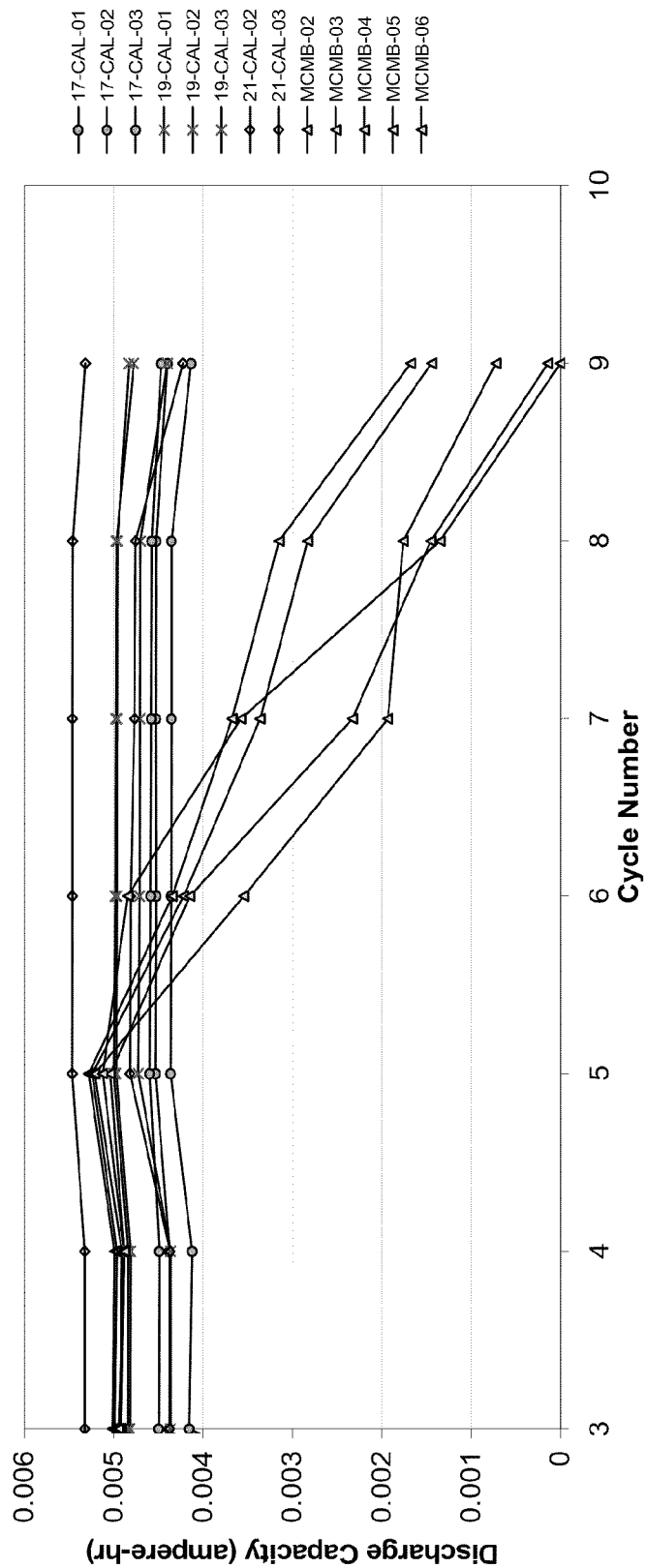
FIG. 12 is a graph illustrating the discharge capacity of battery cells and the effect of overdischarge cycling of such cells.

A graph showing the discharge capacity versus cycle number for each of the cells tested is shown in FIG. 12. Test data revealed a loss of discharge capacity over time after repeated overdischarge cycling for the comparative cells (i.e., cells using carbon active material on copper current collectors), while little or no loss of discharge capacity was observed for cells utilizing $Li_4Ti_5O_{12}$ negative active material and an aluminum foil current collector.

Table 3 lists the cell discharge capacity of the cells during the fourth and ninth cycles of testing (i.e., the cycles immediately preceding and immediately following the overdischarge cycles). For cells using negative electrodes with a $Li_4Ti_5O_{12}$ active material on an aluminum current collector, there is little or no loss in capacity following the overdischarge cycles. For the comparative cells (graphite active material on copper current collector), the average capacity loss was observed to be 84%.

Table 3 also lists the ratio of theoretical capacity of the negative and positive electrodes for the $Li_4Ti_5O_{12}$ cells. This data indicates that little or no capacity loss may be obtained regardless of whether the cells are negative limited (ratio of negative to positive electrode capacity less than 1) or positive limited (ratio of negative to positive electrode capacity greater than 1).

TABLE 3

| Group/ Serial Number | Negative Active Material | Negative/ Positive Electrode Capacity Ratio for $Li_4Ti_5O_{12}$ Cells | Cycle 4 Discharge Capacity (mAh) | Cycle 9 Discharge Capacity (mAh) | Capacity Loss Due to Over-discharge |
|---|---|---|---|---|---|
| 17-CAL-01 | $Li_4Ti_5O_{12}$ | 0.86 | 4.12 | 4.13 | −0.3% |
| 17-CAL-02 | $Li_4Ti_5O_{12}$ | 0.86 | 4.37 | 4.40 | −0.6% |
| 17-CAL-03 | $Li_4Ti_5O_{12}$ | 0.86 | 4.49 | 4.47 | 0.4% |
| | | Average | 4.33 | 4.33 | −0.2% |
| | | Standard Dev. | 0.19 | 0.18 | 0.5% |
| 19-CAL-01 | $Li_4Ti_5O_{12}$ | 0.93 | 4.81 | 4.83 | −0.4% |
| 19-CAL-02 | $Li_4Ti_5O_{12}$ | 0.93 | 4.36 | 4.40 | −0.8% |
| 19-CAL-03 | $Li_4Ti_5O_{12}$ | 0.93 | 4.84 | 4.78 | 1.2% |
| | | Average | 4.67 | 4.67 | 0.0% |
| | | Standard Dev. | 0.27 | 0.24 | 1.1% |
| 21-CAL-02 | $Li_4Ti_5O_{12}$ | 1.02 | 5.32 | 5.32 | 0.1% |
| 21-CAL-03 | $Li_4Ti_5O_{12}$ | 1.02 | 4.37 | 4.23 | 3.2% |
| | | Average | 4.84 | 4.77 | 1.6% |
| | | Standard Dev. | 0.67 | 0.77 | 2.2% |
| MCMB-02 | Carbon | n/a | 4.99 | 1.68 | 66.4% |
| MCMB-03 | Carbon | n/a | 4.96 | 1.44 | 71.0% |
| MCMB-04 | Carbon | n/a | 4.88 | 0.14 | 97.1% |
| MCMB-05 | Carbon | n/a | 4.91 | 0.72 | 85.3% |
| MCMB-06 | Carbon | n/a | 4.88 | 0.00 | 100.0% |
| | | Average | 4.93 | 0.80 | 84.0% |
| | | Standard Dev. | 0.05 | 0.75 | 15.1% |

Figures 13, 14:
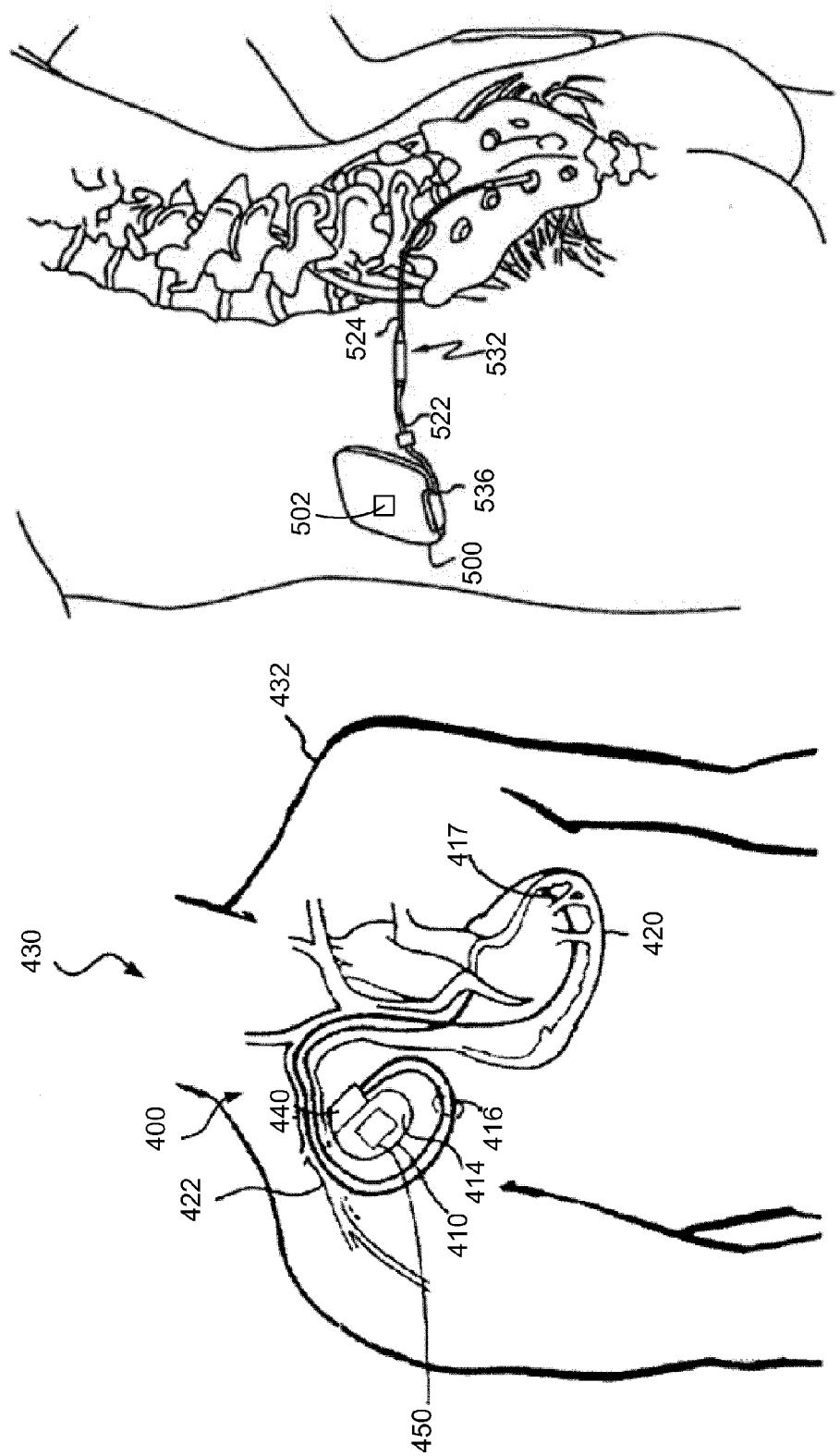
FIG. 13 is a schematic view of a system in the form of an implantable medical device implanted within a body or torso of a patient.
FIG. 14 is a schematic view of another system in the form of an implantable medical device.

The batteries described herein may find utility in a variety of applications, including in implantable medical devices (IMDs). FIG. 13 illustrates a schematic view of a system 400 (e.g., an implantable medical device) implanted within a body or torso 432 of a patient 430. The system 400 includes a device 410 in the form of an implantable medical device that for purposes of illustration is shown as a defibrillator configured to provide a therapeutic high voltage (e.g., 700 volt) treatment for the patient 430.

The device 410 includes a container or housing 414 that is hermetically sealed and biologically inert according to an exemplary embodiment. The container may be made of a conductive material. One or more leads 416 electrically connect the device 410 and to the patient's heart 420 via a vein 422. Electrodes 417 are provided to sense cardiac activity and/or provide an electrical potential to the heart 420. At least a portion of the leads 416 (e.g., an end portion of the leads shown as exposed electrodes 417) may be provided adjacent or in contact with one or more of a ventricle and an atrium of the heart 420.

The device 410 includes a battery 440 provided therein to provide power for the device 410. The size and capacity of the battery 440 may be chosen based on a number of factors, including the amount of charge required for a given patient's physical or medical characteristics, the size or configuration of the device, and any of a variety of other factors. According to an exemplary embodiment, the battery is a 5 mAh battery. According to another exemplary embodiment, the battery is a 300 mAh battery. According to various other exemplary embodiments, the battery may have a capacity of between approximately 1 and 1000 mAh.

According to other exemplary embodiments, more than one battery may be provided to power the device 410. In such exemplary embodiments, the batteries may have the same capacity or one or more of the batteries may have a higher or lower capacity than the other battery or batteries. For example, according to an exemplary embodiment, one of the batteries may have a capacity of approximately 500 mAh while another of the batteries may have a capacity of approximately 75 mAh.

According to an exemplary embodiment, the battery may be configured such that it may be charged and recharged using an inductive charging system in which a primary or external coil is provided at an exterior surface of a portion of the body (either proximate or some distance away from the battery) and a secondary or internal coil is provided below the skin adjacent the primary coil.

According to another exemplary embodiment shown in FIG. 14, an implantable neurological stimulation device 500 (an implantable neuro stimulator or INS) may include a battery 502 such as those described above with respect to the various exemplary embodiments. Examples of some neuro stimulation products and related components are shown and described in a brochure titled "Implantable Neurostimulation Systems" available from Medtronic, Inc.

An INS generates one or more electrical stimulation signals that are used to influence the human nervous system or organs. Electrical contacts carried on the distal end of a lead are placed at the desired stimulation site such as the spine or brain and the proximal end of the lead is connected to the INS. The INS is then surgically implanted into an individual such as into a subcutaneous pocket in the abdomen, pectoral region, or upper buttocks area. A clinician programs the INS with a therapy using a programmer. The therapy configures parameters of the stimulation signal for the specific patient's therapy. An INS can be used to treat conditions such as pain, incontinence, movement disorders such as epilepsy and Parkinson's disease, and sleep apnea. Additional therapies appear promising to treat a variety of physiological, psychological, and emotional conditions. Before an INS is implanted to deliver a therapy, an external screener that replicates some or all of the INS functions is typically connected to the patient to evaluate the efficacy of the proposed therapy.

The INS 500 includes a lead extension 522 and a stimulation lead 524. The stimulation lead 524 is one or more insulated electrical conductors with a connector 532 on the proximal end and electrical contacts (not shown) on the distal end. Some stimulation leads are designed to be inserted into a patient percutaneously, such as the Model 3487A Pisces-Quad® lead available from Medtronic, Inc. of Minneapolis Minn., and stimulation some leads are designed to be surgically implanted, such as the Model 3998 Specify® lead also available from Medtronic.

Although the lead connector 532 can be connected directly to the INS 500 (e.g., at a point 536), typically the lead connector 532 is connected to a lead extension 522. The lead extension 522, such as a Model 7495 available from Medtronic, is then connected to the INS 500.

Implantation of an INS 500 typically begins with implantation of at least one stimulation lead 524, usually while the patient is under a local anesthetic. The stimulation lead 524 can either be percutaneously or surgically implanted. Once the stimulation lead 524 has been implanted and positioned, the stimulation lead's 524 distal end is typically anchored into position to minimize movement of the stimulation lead 524 after implantation. The stimulation lead's 524 proximal end can be configured to connect to a lead extension 522.

The INS 500 is programmed with a therapy and the therapy is often modified to optimize the therapy for the patient (i.e., the INS may be programmed with a plurality of programs or therapies such that an appropriate therapy may be administered in a given situation).

A physician programmer and a patient programmer (not shown) may also be provided to allow a physician or a patient to control the administration of various therapies. A physician programmer, also known as a console programmer, uses telemetry to communicate with the implanted INS 500, so a clinician can program and manage a patient's therapy stored in the INS 500, troubleshoot the patient's INS system, and/or collect data. An example of a physician programmer is a Model 7432 Console Programmer available from Medtronic. A patient programmer also uses telemetry to communicate with the INS 500, so the patient can manage some aspects of her therapy as defined by the clinician. An example of a patient programmer is a Model 7434 Itrel® 3 EZ Patient Programmer available from Medtronic.

According to an exemplary embodiment, a battery provided as part of the INS 500 may be configured such that it may be charged and recharged using an inductive charging system in which a primary or external coil is provided at an exterior surface of a portion of the body (either proximate or some distance away from the battery) and a secondary or internal coil is provided below the skin adjacent the primary coil.

While the medical devices described herein (e.g., systems 400 and 500) are shown and described as a defibrillator and a neurological stimulation device, it should be appreciated that other types of implantable medical devices may be utilized according to other exemplary embodiments, such as pacemakers, cardioverters, cardiac contractility modules, drug administering devices, diagnostic recorders, cochlear implants, and the like for alleviating the adverse effects of various health ailments.

It is also contemplated that the medical devices described herein may be charged or recharged when the medical device is implanted within a patient. That is, according to an exemplary embodiment, there is no need to disconnect or remove the medical device from the patient in order to charge or recharge the medical device.

As utilized herein, the terms "approximately," "about," "substantially", and similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of certain features described and claimed without restricting the scope of these features to the precise numerical ranges provided. Accordingly, these terms should be interpreted as indicating that insubstantial or inconsequential modifications or alterations of the subject matter described and claimed are considered to be within the scope of the invention as recited in the appended claims.

It should be noted that the term "exemplary" as used herein to describe various embodiments is intended to indicate that such embodiments are possible examples, representations, and/or illustrations of possible embodiments (and such term is not intended to connote that such embodiments are necessarily extraordinary or superlative examples).

It is important to note that the construction and arrangement of the batteries and cells and the methods for forming such batteries as shown and described in the various exemplary embodiments is illustrative only. Although only a few embodiments have been described in detail in this disclosure, those skilled in the art who review this disclosure will readily appreciate that many modifications are possible without materially departing from the novel teachings and advantages of the subject matter recited in the claims. Accordingly, all such modifications are intended to be included within the scope of the present invention as defined in the appended claims. The order or sequence of any process or method steps may be varied or re-sequenced according to other exemplary embodiments. Other substitutions, modifications, changes, and omissions may be made in the design, operating conditions, and arrangement of the various exemplary embodiments without departing from the scope of the present inventions as expressed in the appended claims.

What is claimed is:

1. A rechargeable lithium-ion battery comprising:
a housing comprising titanium or a titanium alloy;
a positive electrode having a first capacity and comprising an active material selected from the group consisting of $LiCoO_2$, $LiMn_2O_4$, $LiNiO_2$, $LiCoPO_4$, $LiCoPO_4F$, and $LiFeMn_{2-x}O_4$ (where $0<x<0.5$);
a negative electrode having a second capacity that is less than the first capacity such that the battery has a negative-limited design, the negative electrode comprising a $Li_4Ti_5O_{12}$ active material;
a liquid electrolyte comprising a lithium salt dissolved in at least one non-aqueous solvent; and
a porous polymeric separator located between the positive electrode and negative electrode, wherein the separator is configured to allow lithium ions to flow through the separator;
wherein the negative electrode has a capacity fade rate that is lower than that of the positive electrode.

2. The rechargeable lithium-ion battery of claim 1, wherein the battery has a total irreversible capacity loss after formation of between approximately 12 and 20 percent.

3. The rechargeable lithium-ion battery of claim 1, wherein the battery has a zero volt crossing potential that is above the level where the active material of the positive electrode degrades.

4. The rechargeable lithium-ion battery of claim 1, wherein the liquid electrolyte does not include additives intended to prevent degradation due to oxidation of the positive electrode.

5. The rechargeable lithium-ion battery of claim 1, wherein the $Li_4Ti_5O_{12}$ active material is configured to cycle lithium at a potential of greater than 0.2 volts versus a lithium reference electrode.

6. The rechargeable lithium-ion battery of claim 1, wherein the second capacity is less than approximately ninety percent of the first capacity.

7. The rechargeable lithium-ion battery of claim 1, wherein the electrolyte consists essentially of ethylene carbonate, ethylmethyl carbonate, and a salt of $LiPF_6$.

8. The rechargeable lithium-ion battery of claim 7, wherein the electrolyte does not include additives that are intended to prevent degradation due to oxidation of the positive electrode.

9. The rechargeable lithium-ion battery of claim 1, wherein the electrolyte does not include a molten salt.

10. The rechargeable lithium-ion battery of claim 1, wherein the battery has an intended operating range of between 2.8 volts and 1.8 volts.

11. The rechargeable lithium-ion battery of claim 1, wherein the positive electrode and the negative electrode are wound electrodes.

12. A rechargeable lithium-ion battery comprising:
a positive electrode comprising an active material selected from the group consisting $LiCoO_2$, $LiMn_2O_4$, $LiNiO_2$, $LiCoPO_4$, $LiCoPO_4F$, and $LiFeMn_{2-x}O_4$ (where $0<x<0.5$);
a negative electrode comprising a $Li_4Ti_5O_{12}$ active material that cycles lithium at a potential of greater than 0.2 volts versus a lithium reference electrode;
a liquid electrolyte comprising ethylene carbonate and free of molten salt;
a porous polymeric separator; and
wherein the positive electrode, negative electrode, liquid electrolyte, and porous polymeric separator are within a case formed of a materials selected from the group consisting of titanium and a titanium alloy;
wherein the positive electrode has a first capacity and the negative electrode has a second capacity, the second capacity being less than the first capacity such that the battery is negative-limited, whereby the battery exhibits improved resistance to capacity fade after repeated cycling as compared to batteries having balanced electrode capacities; and
wherein the negative electrode has a capacity fade rate that is lower than that of the positive electrode.

13. The rechargeable lithium-ion battery of claim 12, wherein the battery has a total irreversible capacity loss after formation of between approximately 12 and 20 percent.

14. The rechargeable lithium-ion battery of claim 12, wherein the battery has a zero volt crossing potential that is above the level where the active material of the positive electrode degrades.

15. The rechargeable lithium-ion battery of claim 12, wherein the liquid electrolyte further comprises ethylmethyl carbonate and a salt of $LiPF_6$.

16. The rechargeable lithium-ion battery of claim 15, wherein the liquid electrolyte does not include biphenyl.

17. The rechargeable lithium-ion battery of claim 12, wherein the second capacity is less than approximately ninety percent of the first capacity.

18. The rechargeable lithium-ion battery of claim 12, wherein the positive electrode and the negative electrode are provided as wound electrodes.

19. A rechargeable lithium-ion battery comprising:
a housing comprising titanium or a titanium alloy;
a positive electrode comprising an active material selected from the group consisting $LiCoO_2$, $LiMn_2O_4$, $LiNiO_2$, $LiCoPO_4$, $LiCoPO_4F$, and $LiFeMn_{2-x}O_4$ (where $0<x<0.5$);
a negative electrode comprising a $Li_4Ti_5O_{12}$ active material;

a liquid electrolyte that is free of molten salt; and a porous polymeric separator;

wherein the rechargeable lithium-ion battery has a negative-limited cell balance such that the positive electrode has greater capacity than the negative electrode and wherein the capacity fade rate of the negative electrode is less than that of the positive electrode; and wherein the negative electrode has a capacity fade rate that is lower than that of the positive electrode.

20. The rechargeable lithium-ion battery of claim 19, wherein the rechargeable lithium-ion battery has a total irreversible capacity loss after formation of between approximately 12 and 20 percent.

21. The rechargeable lithium-ion battery of claim 19, wherein the rechargeable lithium-ion battery has a zero volt crossing potential that is above the level where the active material of the positive electrode degrades.

22. The rechargeable lithium-ion battery of claim 19, wherein the liquid electrolyte consists essentially of ethylene carbonate, ethylmethyl carbonate, and a salt of $LiPF_6$.

23. The rechargeable lithium-ion battery of claim 19, wherein the rechargeable lithium-ion battery has an intended operating range of between 2.8 volts and 1.8 volts.

24. The rechargeable lithium-ion battery of claim 19, wherein the positive electrode and the negative electrode are provided as wound electrodes.

* * * * *